United States Patent
Iwakubo et al.

(10) Patent No.: US 7,615,564 B2
(45) Date of Patent: Nov. 10, 2009

(54) ISOQUINOLINE DERIVATIVES HAVING KINASAE INHIBITORY ACTIVITY AND DRUGS CONTAINING THE SAME

(75) Inventors: Masayuki Iwakubo, Saitama-ken (JP); Yuji Okada, Takasaki (JP)

(73) Assignee: Kirin Beer Kabushiki Kaisha, Tokyo-To (JP)

(*) Notice: Subject to any disclaimer, the term of this patent is extended or adjusted under 35 U.S.C. 154(b) by 572 days.

(21) Appl. No.: 10/527,643

(22) PCT Filed: Sep. 12, 2003

(86) PCT No.: PCT/JP03/11733

§ 371 (c)(1), (2), (4) Date: Oct. 13, 2005

(87) PCT Pub. No.: WO2004/024717

PCT Pub. Date: Mar. 25, 2004

(65) Prior Publication Data

US 2006/0167043 A1    Jul. 27, 2006

(30) Foreign Application Priority Data

Sep. 12, 2002    (JP) .............................. 2002-267077

(51) Int. Cl.
*C07D 403/02*    (2006.01)
*A61K 31/4709*    (2006.01)

(52) U.S. Cl. ....................... 514/310; 546/148

(58) Field of Classification Search ........................ None
See application file for complete search history.

(56) References Cited

U.S. PATENT DOCUMENTS 7,217,722 B2 *    5/2007    Takami et al. ............... 514/307

FOREIGN PATENT DOCUMENTS

| WO | 98/06433 | 2/1998 |
| WO | 01/56988 | 8/2001 |

* cited by examiner

*Primary Examiner*—Zinna N Davis
(74) *Attorney, Agent, or Firm*—Oblon, Spivak, McClelland, Maier & Neustadt, L.L.P.

(57) ABSTRACT

An objective of the present invention is to provide compounds having Rho kinase inhibitory activity and useful for the treatment of diseases mediated by Rho kinase. The compounds according to the present invention are those represented by formula (I) or pharmaceutically acceptable salts or solvates thereof:

(I)

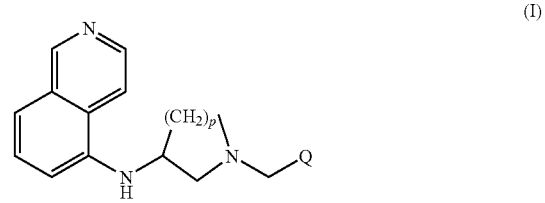

wherein Q represents phenyl, pyridyl, pyrrolyl, thienyl, or furyl; these groups are optionally substituted by one or two halogens or alkyl, nitro, or amino groups; and p is 2 or 3.

11 Claims, No Drawings

ISOQUINOLINE DERIVATIVES HAVING KINASAE INHIBITORY ACTIVITY AND DRUGS CONTAINING THE SAME

This application is a 371 of PCT/JP03/11733 filed Sep. 12, 2003.

BACKGROUND OF THE INVENTION

1. Field of the Invention

The present invention relates to isoquinoline derivatives having Rho kinase inhibitory activity, more particularly to isoquinoline derivatives useful for the treatment of diseases mediated by Rho kinase.

2. Background Art

It has been revealed that Rho is activated upon the receipt of signals from various cell membrane receptors, and the activated Rho functions, through ROCK/Rho kinase and, further, actomyosin system, as a molecular switch of a wide variety of cellular phenomena such as smooth muscle contraction, cell movement, cell adhesion, change in character of cells (formation of actin stressed fibers), control of cell division (sthenia of cytokinesis or activation of gene transcription), platelet aggregation, leukocyte aggregation, cell proliferation, sthenia of carcinogenesis and invasion of cancer and the like.

The contraction of smooth muscle is deeply involved in the pathology of hypertension, angina pectoris, vasospasm, for example, cardiovascular contraction and cerebrovascular contraction, asthma, peripheral circulatory disorder, threatened premature birth, glaucoma, constriction of visual field, pollakiuria, impotence and the like. Cell movement plays an important role in invasion/metastasis of cancer, arteriosclerosis, retinopathy, immune response and the like. Cell adhesion is deeply involved in metastasis of cancer, inflammation, and autoimmune diseases. The change of cell morphology is deeply involved in cerebral dysfunction, osteoporosis, microbism and the like. Cell proliferation is deeply involved in cancer, arteriosclerosis and the like. Thus, Rho is deeply involved in various diseases.

ROCK or ROCK I (Japanese Patent Laid-Open No. 135683/1997; and T Ishizaki et al., EMBO J., Vol. 15, No. 8, pp 1885-1893 (1996)) and Rho kinase or ROCK II (Japanese Patent Laid-Open No. 113187/1998; and T Matsui et al., EMBO J., Vol. 15, No. 9, pp 2208-2216 (1996)) were reported as serine/threonine kinase which is activated upon the activation of Rho and were shown to be isozymes (O. Nakagawa et al., FEBS Lett., Vol. 392, No. 2, pp 189-193 (1996)).

Compounds having ROCK/Rho kinase inhibitory activity include trans-4-amino(alkyl)-1-pyridylcarbamoylcyclohexane compounds (WO 90/05723), benzamide compounds (WO 95/28387), Y-27632 (Uehata, M., Ishizaki, T et al.: Nature, 389: pp 990-994 (1997)), and fasudil hydrochloride commercially available as cerebrovascular contraction inhibitor (HA-1077, Asahi Kasei Kogyo K. K.) (Ono-Saito, N., Niki, I., Hidaka, H.: Pharmacol. Ther., pp 123-131 (1999)). WO 98/06433 discloses ROCK/Rho kinase inhibitors. Further, WO 01/56988 discloses nitrogen-containing compounds having kinase inhibitory activity.

SUMMARY OF THE INVENTION

An object of the present invention is to provide compounds having Rho kinase inhibitory activity and useful for the treatment of diseases mediated by Rho kinase.

Another object of the present invention is to provide a pharmaceutical composition for use in the treatment of diseases mediated by Rho kinase.

The present inventors have found that certain isoquinoline derivatives possess very excellent Rho kinase inhibitory activity (Pharmacological Test Examples 1 and 3). The present inventors have further confirmed that the isoquinoline derivatives are very effective for the treatment of diseases mediated by Rho kinase (Pharmacological Test Examples 2, 4, and 5).

Thus, according to the present invention, there are provided compounds represented by formula (I) or pharmaceutically acceptable salts or solvates thereof:

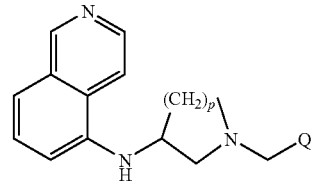

(I)

wherein Q represents a cyclic group selected from phenyl, pyridyl, pyrrolyl, thienyl, and furyl; one or two hydrogen atoms on the cyclic group are optionally substituted by a substituent selected from the group consisting of a halogen atom, $C_{1-4}$ alkyl, nitro, and amino; and p is 2 or 3.

According to another aspect of the present invention, there is provided a pharmaceutical composition comprising the compound according to the present invention as an active ingredient.

DETAILED DESCRIPTION OF THE INVENTION

Compounds

The term "alkyl" as used herein means a straight chain or branched chain alkyl group. Examples of $C_{1-4}$ alkyl include methyl, ethyl, n-propyl, isopropyl, n-butyl, i-butyl, s-butyl, and t-butyl.

The term "halogen atom" means a fluorine, chlorine, bromine, or iodine atom.

Q preferably represents a cyclic group selected from phenyl, 2-chlorophenyl, 3-chlorophenyl, 4-chlorophenyl, 4-fluorophenyl, 2,6-difluorophenyl, 2,6-dichlorophenyl, 4-methylphenyl, 4-isopropylphenyl, 2-nitrophenyl, 3-nitrophenyl, 4-nitrophenyl, 4-chloro-2-nitrophenyl, 2-pyridyl, 3-pyridyl, 4-pyridyl, 2-aminophenyl, 3-aminophenyl, 4-aminophenyl, 2-amino-4-chlorophenyl, 1H-2-pyrrolyl, 1H-3-pyrrolyl, 2-thienyl, 3-thienyl, 2-furyl, and 3-furyl. Particularly preferred are 3-nitrophenyl and 3-aminophenyl.

Examples of preferred compounds represented by formula (I) include compounds in which Q represents 3-nitrophenyl or 3-aminophenyl and p is 2.

Examples of more preferred compounds represented by formula (I) include the following compounds:
(1) N5-[1-(2-chlorobenzyl)tetrahydro-1H-3-pyrrolyl]-5-isoquinolylamine;
(2) N5-[1-(3-chlorobenzyl)tetrahydro-1H-3-pyrrolyl]-5-isoquinolylamine;
(3) N5-[1-(4-chlorobenzyl)tetrahydro-1H-3-pyrrolyl]-5-isoquinolylamine;
(4) N5-[1-(4-fluorobenzyl)tetrahydro-1H-3-pyrrolyl]-5-isoquinolylamine;

(5) N5-[1-(2,6-difluorobenzyl)tetrahydro-1H-3-pyrrolyl]-5-isoquinolylamine;
(6) N5-[1-(2,6-dichlorobenzyl)tetrahydro-1H-3-pyrrolyl]-5-isoquinolylamine;
(7) N-(5-isoquinolyl)-N-[1-(4-methylbenzyl)tetrahydro-1H-3-pyrrolyl]amine;
(8) N5-[1-(4-isopropylbenzyl)tetrahydro-1H-3-pyrrolyl]-5-isoquinolylamine;
(9) N-(5-isoquinolyl)-N-[1-(2-nitrobenzyl)tetrahydro-1H-3-pyrrolyl]amine;
(10) N-(5-isoquinolyl)-N-[1-(3-nitrobenzyl)tetrahydro-1H-3-pyrrolyl]amine;
(11) N-(5-isoquinolyl)-N-[1-(4-nitrobenzyl)tetrahydro-1H-3-pyrrolyl]amine;
(12) N5-[1-(4-chloro-2-nitrobenzyl)tetrahydro-1H-3-pyrrolyl]-5-isoquinolylamine;
(13) N-(5-isoquinolyl)-N-[1-(2-pyridylmethyl)tetrahydro-1H-3-pyrrolyl]amine;
(14) N-(5-isoquinolyl)-N-[1-(3-pyridylmethyl)tetrahydro-1H-3-pyrrolyl]amine;
(15) N-(5-isoquinolyl)-N-[1-(4-pyridylmethyl)tetrahydro-1H-3-pyrrolyl]amine;
(16) N5-[1-(2-aminobenzyl)tetrahydro-1H-3-pyrrolyl]-5-isoquinolylamine;
(17) N5-[1-(3-aminobenzyl)tetrahydro-1H-3-pyrrolyl]-5-isoquinolylamine;
(18) N5-[1-(4-aminobenzyl)tetrahydro-1H-3-pyrrolyl]-5-isoquinolylamine;
(19) N5-[1-(2-amino-4-chlorobenzyl)tetrahydro-1H-3-pyrrolyl]-5-isoquinolylamine;
(20) N5-[1-(2-chlorobenzyl)-3-piperidyl]-5-isoquinolylamine;
(21) N5-[1-(3-chlorobenzyl)-3-piperidyl]-5-isoquinolylamine;
(22) N5-[1-(4-chlorobenzyl)-3-piperidyl]-5-isoquinolylamine;
(23) N-(1-benzyl-3-piperidyl)-5-isoquinolylamine;
(24) N5-[1-(2,6-difluorobenzyl)-3-piperidyl]-5-isoquinolylamine;
(25) N5-[1-(2,6-dichlorobenzyl)-3-piperidyl]-5-isoquinolylamine;
(26) N-(5-isoquinolinyl)-N-[1-(4-methylbenzyl)-3-piperidyl]amine;
(27) N-(5-isoquinolinyl)-N-[1-(4-isopropylbenzyl)-3-piperidyl]amine;
(28) N-(5-isoquinolinyl)-N-[1-(2-nitrobenzyl)-3-piperidyl]amine;
(29) N-(5-isoquinolinyl)-N-[1-(3-nitrobenzyl)-3-piperidyl]amine;
(30) N-(5-isoquinolinyl)-N-[1-(4-nitrobenzyl)-3-piperidyl]amine;
(31) N5-[1-(4-chloro-2-nitrobenzyl)-3-piperidyl]-5-isoquinolylamine;
(32) N-(5-isoquinolinyl)-N-[1-(2-pyridylmethyl)-3-piperidyl]amine;
(33) N-(5-isoquinolinyl)-N-[1-(3-pyridylmethyl)-3-piperidyl]amine;
(34) N-(5-isoquinolinyl)-N-[1-(4-pyridylmethyl)-3-piperidyl]amine;
(35) N5-[1-(2-aminobenzyl)-3-piperidyl]-5-isoquinolylamine;
(36) N5-[1-(3-aminobenzyl)-3-piperidyl]-5-isoquinolylamine;
(37) N5-[1-(4-aminobenzyl)-3-piperidyl]-5-isoquinolylamine;
(38) N5-[1-(2-amino-4-chlorobenzyl)-3-piperidyl]-5-isoquinolylamine;
(39) N-(5-isoquinolinyl)-N-[1-(1H-2-pyrrolylmethyl)-3-piperidyl]amine;
(40) N-(5-isoquinolinyl)-N-[1-(1H-3-pyrrolylmethyl)-3-piperidyl]amine;
(41) N-(5-isoquinolinyl)-N-[1-(2-thienylmethyl)-3-piperidyl]amine;
(42) N-(5-isoquinolinyl)-N-[1-(3-thienylmethyl)-3-piperidyl]amine;
(43) N-[1-(2-furylmethyl)-3-piperidyl]-N-(5-isoquinolyl)amine;
(44) N-[1-(3-furylmethyl)-3-piperidyl]-N-(5-isoquinolyl)amine;
(45) (3S)-N5-[1-(3-aminobenzyl)tetrahydro-1H-3-pyrrolyl]-5-isoquinolineamine; and
(46) (3R)-N5-[1-(3-aminobenzyl)tetrahydro-1H-3-pyrrolyl]-5-isoquinolineamine.

Examples of particularly preferred compounds among the compounds represented by formula (I) include (3S)-N5-[1-(3-aminobenzyl)tetrahydro-1H-3-pyrrolyl]-5-isoquinolineamine and (3R)-N5-[1-(3-aminobenzyl)tetrahydro-1H-3-pyrrolyl]-5-isoquinolineamine and mixtures thereof.

Pharmaceutically acceptable salts of the compounds represented by formula (I) include acid addition salts. Acid addition salts include: salts with inorganic acids such as hydrochloric acid, sulfuric acid, phosphoric acid, hydrobromic acid, and nitric acid; salts with organic acids such as maleic acid, fumaric acid, malic acid, oxalic acid, tartaric acid, succinic acid, citric acid, acetic acid, lactic acid, methanesulfonic acid, p-toluenesulfonic acid and salicylic acid; and salts with amino acids such as lysine. These acid addition salts may be converted to corresponding free bases by a conventional method, for example, by a reaction with an alkali such as sodium hydroxide or potassium hydroxide. Further, the compounds may be brought to quaternary ammonium salts or salts with metals such as sodium, potassium, calcium, magnesium, or aluminum.

Pharmaceutically acceptable solvates of the compounds represented by formula (I) include hydrates.

In the compounds represented by formula (I), optical isomers, racemic forms thereof, and cis and trans isomers may exist, and the compounds according to the present invention include all of these isomers. These isomers may be isolated according to a conventional method, or may be produced by using various materials for respective isomers.

Production of Compounds

The compounds according to the present invention may be produced according to schemes below.

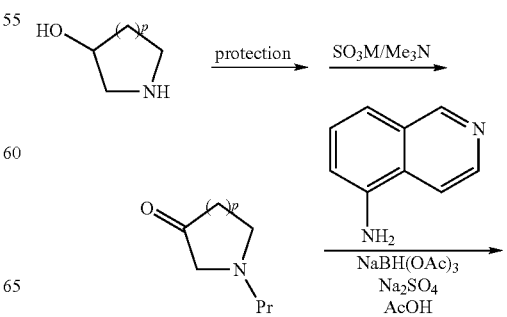

Scheme 1

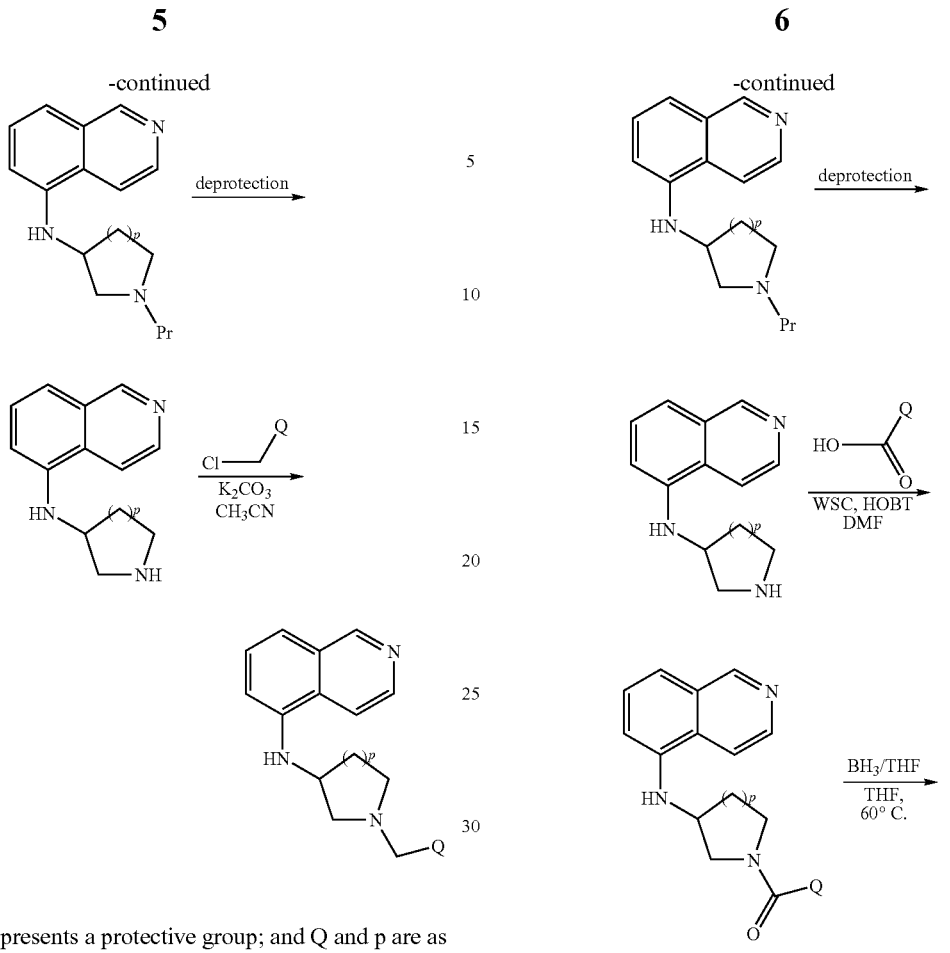

wherein Pr represents a protective group; and Q and p are as defined in formula (I).

The compound in which Q represents phenyl may be produced by protecting the secondary amine of (R)-(−)-3-pyrrolidinol, where p=1, or 3-hydroxypiperidine, where p=2, with a suitable functional group, for example, tert-butyloxycarbony, then oxidizing the protected compound with a sulfur trioxide/trimethylamine complex in DMSO at room temperature, condensing the oxidized compound with 5-aminoisoquinoline in acetic acid in the presence of anhydrous sodium sulfate, reducing the condensate with sodium hydride triacetate to give an intermediate, deprotecting the intermediate, for example, with trifluoroacetic acid, and then reacting the deprotected compound with an alkyl chloride Q-CH$_2$—Cl in the presence of a base, for example, potassium carbonate.

Scheme 2

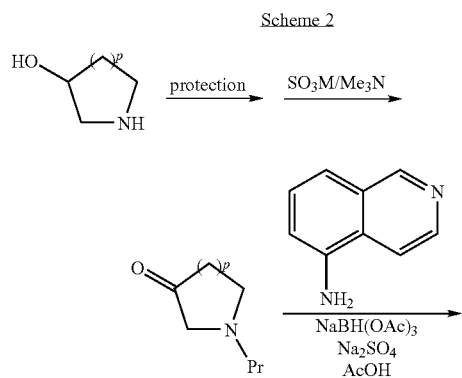

wherein Pr represents a protective group; and Q and p are as defined in formula (I).

The compound in which Q represents pyrrolyl, thienyl, or furyl may be produced by protecting a secondary amine in (R)-(−)-3-pyrrolidinol, where p=1, or 3-hydroxypiperidine, where p=2, with a suitable functional group, for example, tert-butyloxycarbony, then oxidizing the protected compound with sulfur trioxide/trimethylamine complex in DMSO at room temperature, condensing the oxidized compound with 5-aminoisoquinoline in acetic acid in the presence of anhydrous sodium sulfate, reducing the condensate with sodium hydride triacetate to give an intermediate, deprotecting the intermediate, for example, with trifluoroacetic acid, then condensing the deprotected compound with a carboxylic acid Q-COOH using N-[3-(diethylamino)propyl]-N'-ethyl carbodiimide hydrochloride and 1-hydroxybenzotriazole, and subsequently reducing the condensate with a borane/tetrahydrofuran complex.

Scheme 3

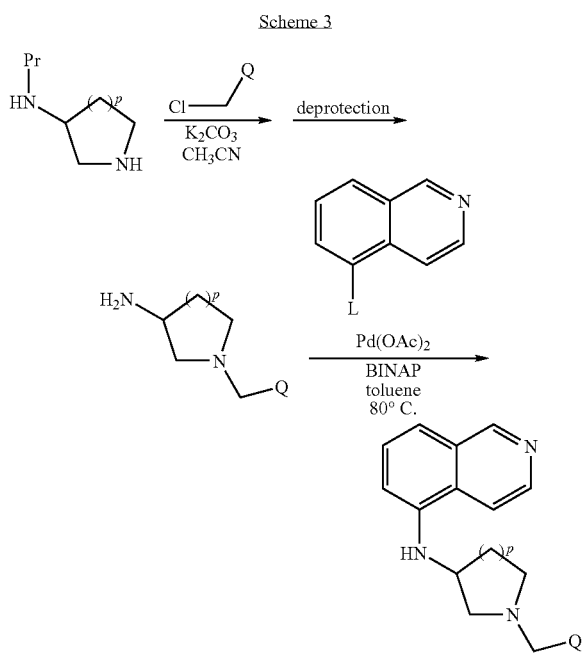

wherein Pr represents a protective group; L represents a leaving group; and Q and p are as defined in formula (I).

These compounds may be produced by reacting the secondary amine of 3-aminopyrrolidine, where p=1, or 3-aminopiperidine, where p=2, in which a primary amine has been protected with a suitable protective group, for example, (3R)-(+)-3-(tert-butoxyamino)pyrrolidine), with an alkyl chloride Q-CH$_2$—Cl in the presence of a base, for example, potassium carbonate, deprotecting the reaction product, for example, with trifluoroacetic acid, and then adding a catalytic amount of palladium acetate and BINAP to the deprotected compound and an isoquinoline having a leaving group X (for example, when X represents triflate, this isoquinoline may be produced by reacting 5-hydroxyisoquinoline with trifluoromethanesulfonic anhydride) in toluene in the presence of cesium carbonate at 80° C.

The compound according to the present invention may also be produced by the method described in WO 01/56988.

Use of Compounds/Pharmaceutical Composition

The compounds according to the present invention have Rho kinase inhibitory activity (see Pharmacological Test Examples 1 and 3). Therefore, the compounds represented by formula (I) can be used in the treatment of diseases mediated by Rho kinase. Diseases mediated by Rho kinase include hypertension, asthma including bronchial asthma, angina pectoris, cerebrovascular contraction, peripheral circulatory disorder, threatened premature birth, glaucoma, constriction of visual field, pollakiuria, cancer, invasion/metastasis of cancer, arteriosclerosis, retinopathy, immune response, inflammation, autoimmune diseases, cerebral dysfunction, osteoporosis, microbism, chronic renal failure, chronic nephritis, diabetic nephropathy, IgA nephropathia, thrombosis-related diseases, rheumatism, impotence, and fibrosis.

According to the present invention, there is provided a method for the treatment of a disease mediated by Rho kinase, comprising the step of administering a therapeutically effective amount of a compound according to the present invention together with a pharmaceutically acceptable carrier, to a mammal including a human.

Further, according to the present invention, there is also provided use of a compound according to the present invention, for the manufacture of a medicament in the treatment of diseases mediated by Rho kinase.

<Hypertension, Asthma, Etc.>

It has been revealed that Rho is activated upon the receipt of signals from various cell membrane acceptors and the activated Rho functions in the contraction of smooth muscle through ROCK/Rho kinase and, further, actomyosin system (K. Kimura et al., Science, Vol. 273, No. 5272, pp 245-248 (1996); and Kureishi et al., J. Biol. Chem., Vol. 272, No. 19, pp 12257-60 (1997)). The contraction of smooth muscle is deeply involved in the pathology of hypertension, angina pectoris, cerebrovascular contraction, asthma, peripheral circulatory disorder, threatened premature birth, glaucoma, constriction of visual field, impotence, pollakiuria, and the like (for example, hypertension: A P. Samlyo et al., Rev. Physiol. Biochem. Pharmacol., Vol. 134, pp 209-34 (1999), angina pectoris: Shimokawa et al., Cardiovasc. Res., Vol. 43, No. 4, pp 1029-39 (1999); and Satoh, H., & Kawahara, K: Jpn. J. Pharmacol., 79 (suppl): 211 P, 1999, cerebrovascular contraction: Motohiko Sato and Kohzo Kaibuchi: Abstract of the 57th Annual Meeting of the Japan Neurosurgical Society: 153, 1998; N. Ono et al., Pharmacol. Ther., Vol. 82, No. 2-3, pp 123-31(1991); and Shimokawa et al., Cardiovasc. Res., Vol. 43, No. 4, pp 1029-39 (1999), impotence: Andersson, K. E. & Stief, C. G. & World J. Vrol. 15, 14-20 (1997)).

For hypertension, ROCK/Rho kinase inhibitors have pressure depression activity in spontaneously hypertensive rats (SHR), two-kidney hypertensive rats, and brine deoxycorticosterone acetate rats (DOCA rats) (Uehata, M., Ishizaki, T. et al.: Nature, 389: 990-994, 1997).

For asthma, ROCK/Rho kinase inhibitors have bronchodilation activity and antiasthmatic activity in extirpated bronchia or bronchial asthma model animals (WO 93/05021 and WO 95/28387). Further, Rho kinase inhibitors suppress an increase in bronchial resistance caused by acetylcholine inhalation in bronchial asthma models in a dose-dependent manner and suppress, in vitro, chemotaxis caused by PAF in eosinophilic leukocytes of human peripheral blood in a concentration-dependent manner (Kunihiko Iitsuka: Arerugi (Allergy), 47: 943, 1998, Kunihiko Iitsuka and Akihiro Yoshii: Journal of The Japanese Respiratory Society, 37: 196, 1999). Further, Rho kinase is also involved in migration of leukocytes.

For glaucoma, it is known that ROCK/Rho kinase inhibitors are involved in trabecular meshwork of rabbits and bovines induced by carbachol and ciliary muscle contraction of rabbits and humans (M. Honjo et al., Investigative Ophthalmology and Visual Science. 2001; 42: 137-144, and T. Hukigami et al., Biochem Biophys Res Commun. 2001 Oct. 26; 288 (2): 296-300) to lower the ocular. tension of rabbits (WO 00/09162 and M. Waki et al., Current Eye Research 2001, Vol. 22, No. 6, pp. 470-474).

For impotence, ROCK/Rho kinase inhibitors have rat corpus carvernosum penis relaxation activity in vitro and have rat corpus carvernosum penis pressure rising activity in vitro (Kanchan Chitaley et al., Nature Medicine, Vol. 7, No. 1, 119-122 (2001)).

The compounds according to the present invention actually have leukocyte migration inhibitory activity and blood pressure depression activity (see Pharmacological Test Examples 2 and 5).

Therefore, the compounds according to the present invention can be used in the treatment of hypertension, asthma including bronchial asthma, angina pectoris, cerebrovascular contraction, peripheral circulatory disorder, threatened premature birth, glaucoma, constriction of visual field, impotence, pollakiuria and other diseases.

<Cancer, Metastasis of Cancer, Etc.>

Rho is activated upon the receipt of signals from various cell membrane acceptors, and the activated Rho functions, through ROCK/Rho kinase and, further, actomyosin system, as a molecular switch of cellular phenomena such as cell movement, cell adhesion, alteration of cytoplasm (formation of actin stressed fibers), control of cell division (sthenia of cytokinesis or activation of gene transcription), cell proliferation, sthenia of carcinogenesis and invasion of cancer and the like (P. Keely et al., Trends Cell Biol. Vol. 8, No. 3, pp 101-6 (1998); and K. Itoh et al., Nat. Med., Vol. 5, No. 2, pp 221-5 (1999)).

Cell movement plays an important role in invasion/metastasis of cancer, arteriosclerosis, retinopathy, immune response and the like. Cell adhesion is deeply involved in metastasis of cancer, inflammation, and autoimmune diseases. The cytoskeletal change is deeply involved in cerebral dysfunction, osteoporosis, microbism and the like. Cell proliferation is deeply involved in cancer, arteriosclerosis and the like (Experimental Medicine), Vol. 17, No. 7 (1999)).

In particular, for transformation of cells to malignant state and metastasis/invasion of cancer, Rho is involved in the control of cell morphology and, in addition, in cell proliferation, particularly in the progression of cell cycle from gap1 period (G1 phase) to synthesis period (S phase) (Yamamoto, M., Marui, N., Oncogene, 8: 1449-1455, 1993). Further, it has been found that oncogenes such as Dbl are GDP-GTP exchange factors for Rho family (Hart, M. J., Eva, A., Nature, 354: 311-314, 1991). Further, it has been found that Rac and Rho are activated downstream of information transmission of Ras (Ridley, A. J. & Hall, A.: Cell, 70: 401-410, 1992). Further, it is reported that Rac and Rho are in the downstream of Ras, and involved in the transformation of cancer cells to malignant state by Ras (Qui, R. G., Chen, J., et al.: Nature, 374: 457-459, 1995, Qui, R. G., Chen, J., et al.: Proc. Natl. Acad. Sci. USA, 92: 11781-11785, 1995, and Khosravi-Far, R., Solski, P. A.: Mol. Cell. Biol., 15: 6443-6453, 1995). Furthermore, it has been proven by ROCK/Rho kinase inhibitor (Y-27632) that the path from Rho to ROCK is involved in transformation of cancer cells to malignant state (Sahai, E., Ishizaki, T: Curr. Biol., 9: 136-145, 1999).

Further, it is reported in various cell systems that, as with leukocytes, cell movement in cancer invasion is regulated by an actomyosin system as a moving device and an intracellular signal transfer system for controlling the actomyosin system and Rho family protein regulates cytoskeleton protein and controls various cell functions such as alteration of morphology, adhesion, movement, division, transfer regulation and the like of cells (K. Itoh et al., Nat. Med., Vol. 5, No. 2, pp 221-5 (1999); P. Keely et al., Trends Cell Biol. Vol. 8, No. 3, pp 101-6 (1998)).

It is also reported that ROCK downstream of Rho controls invasive movement through the activation of an actomyosin system (Yoshioka, K., Matsumura, F.: J. Biol. Chem., 273: 5146-5154, 1998). It has been demonstrated that controlling the path from Rho to ROCK by ROCK/Rho kinase inhibitor (Y-27632) suppresses the invasive movement (Itoh, K., Yoshioka, K.: Nature Med., 5: 221-225, 1999).

Therefore, the compounds according to the present invention can be used in treatment of cancer, invasion/metastasis of cancer, arteriosclerosis, retinopathy, immune response, inflammation, autoimmune diseases, cerebral dysfunction, osteoporosis, and microbism.

<Renal Diseases>

Renal disorder was found in Rho GDI knockout mouse (Oncogene, 1999; 18 (39): 5373-80).

Further, as described above, Rho is activated upon the receipt of signals from various cell membrane acceptors, and the activated Rho is involved in cell adhesion or migration of leukocytes through ROCK/Rho kinase and actomyosin system. Cell adhesion and migration of leukocytes are involved in inflammation, particularly nephritis (Osamu Fujimoto and Kohzo Kaibuchi, Journal of The Japanese Society of Internal Medicine, 1999; 88 (1); 148-54).

Furthermore, Rho is involved in nephritis through HGF, oxidized LDL, platelets, or Na—H exchange (Mol. Cell. Biol. 1995; 15 (2): 1110-22; J. Biol. Chem. 1999; 274 (43): 30361-4; J. Biol. Chem., 1999; 274 (40): 28293-300; and EMBO J., 1998; 17 (16): 4712-22).

The compounds according to the present invention actually have proteinuria amelioration activity (see Pharmacological Test Example 4).

Therefore, the compounds according to the present invention can be used in the treatment of chronic renal failure, chronic nephritis, diabetic nephropathy, and IgA nephropathia.

<Inflammation, Thrombosis-related Diseases, Etc.>

It is known that Rho is activated upon the receipt of signals from various cell membrane acceptors, and the activated Rho functions, through Rho kinase and, further, actomyosin system, as a molecular switch of cellular phenomena such as platelet aggregation, leukocyte aggregation, and leukocyte migration (K. Naka et al., Blood, Vol. 90, No. 10, pp 3736-42 (1997)). Platelet aggregation, leukocyte aggregation, and leukocyte migration are deeply involved in thrombus, inflammation, fibrosis and the like.

The compounds according to the present invention actually have leukocyte migration inhibitory activity (see Pharmacological Test Example 2).

Therefore, the compounds according to the present invention can be used in the treatment of inflammation, asthma, thrombosis-related diseases, for example, cardiac infarction, cerebral infarction, arteriosclerosis obliterans, thrombus obstruction, and generalized angiocoagulation syndrome, rheumatism, and fibrosis.

Pharmaceutical compositions comprising compounds of the present invention as an active ingredient can be administered to human and non-human animals orally or parenterally by administration routes, for example, intravenous administration, intramuscular administration, subcutaneous administration, rectal administration, or percutaneous administration. Therefore, the pharmaceutical composition comprising a compound according to the present invention as an active ingredient may be formulated into suitable dosage forms according to the administration routes.

Specifically, oral preparations include tablets, capsules, powders, granules, syrups, pills, and troches, and parental preparations include injections, such as solutions and suspensions, inhalants, suppositories, transdermal preparations, for example, tapes, ointments, eye drops, and eye ointments.

These various preparations may be prepared by conventional methods, for example, with commonly used component, such as excipients, disintegrants, binders, lubricants, colorants, diluents, corrigents, flavors, emulsifiers, and solubilizers.

Excipients include, for example, lactose, glucose, corn starch, sorbit, and crystalline cellulose. Disintegrants include, for example, starch, sodium alginate, gelatin powder, calcium carbonate, calcium citrate, and dextrin. Binders include, for example, dimethylcellulose, polyvinyl alcohol, polyvinyl ether, methylcellulose, ethylcellulose, gum arabic, gelatin, hydroxypropylcellulose, and polyvinyl pyrrolidone. Lubricants include, for example, talc, magnesium stearate, polyethylene glycol, and hydrogenated vegetable oils.

In the formulation of solid preparations, additives are used such as sucrose, lactose, cellulose sugar, D-mannitol, maltitol, dextran, starches, agar, alginates, chitins, chitosans, pectins, tragacanths, gum arabics, gelatins, collagens, caseins, albumin, calcium phosphate, sorbitol, glycine, carboxymethylcellulose, polyvinyl pyrrolidone, hydroxypropylcellulose, hydroxypropylmethylcellulose, glycerin, polyethylene glycol, sodium hydrogencarbonate, magnesium stearate, and talc. Further, tablets may be those on which, if necessary, conventional coating has been provided, for example, sugar coated tablets, enteric coated tablets, film coated tablets, or two-layer tablets, and multilayer tablets.

In the formulation of semi-solid preparations, vegetable fats and oils, such as olive oils, corn oils, and castor oils, mineral fats and oils, such as petrolatum, white petrolatum, and hard paraffin, waxes, such as jojoba oils, carnauba wax, and beeswax, and partially synthesized or wholly synthesized glycerin fatty acid esters, such as laurylic acid, myristic acid, and palmitic acid, and the like may be used. Examples of commercially available products thereof include Witepsol manufactured by Dynamid Nobel and Pharmasol manufactured by Nippon Oils & Fats Co., Ltd.

In the formulation of solutions, additives may be used such as sodium chloride, glucose, sorbitol, glycerin, olive oil, propylene glycol, and ethyl alcohol. In the formulation of injections, aseptic aqueous solutions, for example, physiological saline, isotonic solutions, oily solutions, for example, sesame oils and soybean oils, may be used. If necessary, suitable suspending agents, for example, sodium carboxymethylcellulose, nonionic surfactants, solubilizers, for example, benzyl benzoate, benzyl alcohol and the like may be used in combination with the above solutions.

In the formulation of eye drops, aqueous liquid preparations or aqueous solutions are used, and, in particular, aseptic aqueous solutions for injections may be used. Various additives, such as buffers, preferably, for example, borate buffers, acetate buffers, and carbonate buffers for abatement of stimulation, isotonicity, solubilizers, preservatives, thickening agents, chelating agents, pH adjustors (in general, pH being preferably adjusted to about 2 to 8.5), and aromatics, may be properly added to the liquid preparation for eye drops.

The content of a compound according to the present invention in the pharmaceutical composition may vary according to the dosage form. The content is, however, generally about 0.1 to 100% by weight, preferably about 1 to 50% by weight, based on the whole composition.

The dose may be appropriately determined in consideration of particular conditions, for example, the age, weight, sex, type of disease, and severity of condition of patients, and the preparation may be administered, for example, in an amount of about 1 to 500 mg. This dose may be administered at a time daily or divided doses of several times daily.

EXAMPLES

The present invention is further illustrated by the following Examples that are not intended as a limitation of the invention.

Intermediate 1: Tert-butyl 3-(5-isoquinolylamino)-1-pyrrolidinecarboxylate (R)-pyrrolidinol (Tokyo Chemical Industry Co., Ltd., 12.4 g, 100 mmol) was dissolved in 100 ml of a 3 N aqueous solution of sodium hydroxide. A solution (50 ml) of di-tert-butyl dicarbonate (Tokyo Chemical Industry Co., Ltd., 25.0 g, 120 mmol) in tetrahydrofuran was added dropwise thereto at 0° C. The pH value of the mixture was determined with a pH test paper and was found to be 11. The mixture was then stirred at room temperature for 2 hr and was then concentrated to remove a major part of tetrahydrofuran. The aqueous layer was extracted three times with ethylacetate. The combined organic layer was dried over sodium sulfate and was concentrated to give a crude product.

The crude product and triethylamine (20 ml) were dissolved in anhydrous dimethylsulfoxide (100 ml), and a triturated sulfur trioxide/trimethylamine complex (Aldrich, 28.0 g, 200 mmol) was added little by little thereto at room temperature. The mixture was stirred at room temperature for 18 hr. Water (200 ml) was then added to the reaction solution to stop the reaction. The aqueous layer was extracted three times with ethylacetate. The combined organic layer was dried over sodium sulfate and was concentrated to give a crude product.

The crude product was loaded on a silica gel column and developed with chloroform, followed by development with chloroform only to give an intermediate (11.25 g).

The intermediate (3.70 g, 20 mmol) and 5-aminoisoquinoline (Aldrich, 2.48 g, 17 mmol) were dissolved in 100 ml of acetic acid. Sodium sulfate (14.2 g, 100 mmol) was added thereto, and the mixture was stirred at room temperature for 30 min. The reaction mixture was cooled to 0° C., sodium hydride triacetate (Aldrich, 4.44 g, 20 mmol) was added thereto little by little, and the mixture was stirred at room temperature for 18 hr. The reaction solution was concentrated under the reduced pressure to remove a major part of acetic acid. The reaction mixture was then adjusted to pH=8 by the addition of a saturated sodium hydrogencarbonate solution and was filtered through Celite, and the filtrate was separated into an organic layer and an aqueous layer. The aqueous layer was extracted three times with ethylacetate. The combined organic layer was dried over sodium sulfate and was concentrated to give a crude product.

The crude product in methylene chloride was loaded on a silica gel column and developed with hexane. The development was first carried out with hexane only, subsequently with hexane/chloroform (1:1), and finally with chloroform only to collect a fraction having UV absorption with Rf=0.6 to give the title compound (3.70 g, 12 mmol).

$^1$H-NMR (CDCl$_3$, 400 MHz): 1.46 (s, 9H), 1.75-1.94 (m, 1H), 2.02-2.10 (m, 1H), 3.35-3.55 (m, 31H), 3.75-3.86 (m, 1H), 4.17-4.24 (m, 1H), 4.705-4.90 (m, 1H), 6.91 (d, J=7.6 Hz, 1H), 7.44 (d, J=8.3 Hz, 1H), 7.58 (t, J=7.9 Hz, 1H), 7.80-7.90 (m, 1H), 8.42 (d, J=6.4 Hz, 1H), 9.20 (s, 1H).

Mass spectrometric value (ESI-MS, m/z): 314 (M$^+$+1)

Intermediate 2: Tert-butyl 3-(5-isoquinolylamino)-1-piperidine-carboxylate (R)-pyrrolidinol (Tokyo Chemical Industry Co., Ltd., 12.4 g, 100 mmol) was dissolved in 100 ml of a 3 N aqueous solution of sodium hydroxide. A solution (50 ml) of di-tert-butyl dicarbonate (Tokyo Chemical Industry Co., Ltd., 25.0 g, 120 mmol) in tetrahydrofuran was added dropwise thereto at 0° C. The pH value of the mixture was confirmed to be 11 with a pH test paper. The mixture was stirred at room temperature for 2 hr and was then concentrated to remove a major part of tetrahydrofuran. The aqueous layer was extracted three times with ethylacetate. The combined organic layer was dried over sodium sulfate and was concentrated to give a crude product.

The crude product and triethylamine (20 ml) were dissolved in anhydrous dimethylsulfoxide (100 ml). Finely triturated sulfur trioxide/trimethylamine complex (Aldrich, 28.0 g, 200 mmol) was added thereto little by little at room temperature. The mixture was stirred at room temperature for 18 hr. Thereafter, 200 ml of water was added to stop the reaction. The aqueous layer was extracted three times with ethylacetate. The combined organic layer was dried over sodium sulfate and was concentrated to give a crude product.

The crude product was purified by a silica gel column eluted with chloroform. The development was carried out with chloroform to give an intermediate (15.6 g).

The intermediate (3.70 g, 20 mmol) and 5-aminoisoquinoline (Aldrich, 2.48 g, 17 mmol) were dissolved in 100 ml of acetic acid. Sodium sulfate (14.2 g, 100 mmol) was added thereto, and the mixture was stirred at room temperature for 30 min. The reaction mixture was cooled to 0° C. Sodium hydride triacetate (Aldrich, 4.44 g, 20 mmol) was added thereto little by little, and the mixture was stirred at room temperature for 18 hr. The reaction solution was concentrated under the reduced pressure to remove a major part of acetic acid. The reaction mixture was then adjusted to pH 8 by the addition of a saturated sodium hydrogencarbonate solution and was filtered through Celite, and the filtrate was separated into an organic layer and an aqueous layer. The aqueous layer was extracted three times with ethylacetate, The combined organic layer was dried over sodium sulfate and was concentrated to give a crude product.

The crude product dissolved in methylene chloride was purified by a silica gel column and developed with hexane. The development was first carried out with hexane only, then with hexane/chloroform (1:1), and finally with chloroform only to collect a fraction having UV absorption with Rf=0.6 to give the title compound (3.720 g, 12 mmol).

$^1$H-NMR (CDCl$_3$, 400 MHz): 1.44 (s, 9H), 1.48-1.68 (m, 1H), 1.73-1.83 (m, 2H), 1.90-2.10 (m, 1H), 3.10-3.32 (m, 2H), 3.52-3.65 (m, 2H), 3.92-3.98 (m, 1H), 6.86 (d, J=7.6 Hz, 1H), 7.30 (d, J=8.3 Hz, 1H), 7.45 (t, J=7.9 Hz, 1H), 7.54 (d, J=5.8 Hz, 1H), 8.42 (d, J=5.8 Hz, 1H), 9.13 (s, 1H).

Mass spectrometric value (ESI-MS, m/z): 328 (M$^+$+1)

Example 1

N5-[1-(2-Chlorobenzyl)tetrahydro-1H-3-pyrrolyl]-5-isoquinolylamine

Tert-butyl 3-(5-isoquinolylamino)-1-pyrrolidinecarboxylate (intermediate 1) (62 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in 1 ml of acetonitrile. A solution (1 ml) of 2-chlorobenzylchloride (40 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give the title compound (28 mg, 0.083 mmol).

$^1$H-NMR (CDCl$_3$, 400 MHz): 1.98-2.10 (m, 1H), 2.40-2.52 (m, 1H), 2.70-2.90 (m, 1H), 3.00-3.86 (m, 3H), 4.00-4.15 (m, 2H), 4.25-4.35 (m, 1H), 6.59 (d, J=7.6 Hz, 1H), 7.20-7.28 (m, 3H), 7.32-7.38 (m, 2H), 7.63-7.83 (m, 2H), 8.44 (d, J=5.8 Hz, 1H), 9.07 (s, 1H).

Mass spectrometric value (ESI-MS, m/z): 339 (M$^+$+1)

Example 2

N5-[1-(3-Chlorobenzyl)tetrahydro-1H-3-pyrrolyl]-5-isoquinolylamine

Tert-butyl 3-(5-isoquinolylamino)-1-pyrrolidinecarboxylate (intermediate 1) (62 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in 1 ml of acetonitrile. A solution (1 ml) of 3-chlorobenzylchloride (40 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give the title compound (14 mg, 0.042 mmol).

$^1$H-NMR (CDCl$_3$, 400 MHz): 2.00-2.10 (m, 1H), 2.45-2.55 (m, 1H), 2.70-2.80 (m, 1H), 3.00-3.45 (m, 3H), 3.80-3.90 (m, 2H), 4.25-4.36 (m, 1H), 6.64 (d, J=7.6 Hz, 1H), 7.28-7.34 (m, 3H), 7.37-7.43 (m, 3H), 7.75-7.85 (m, 1H), 8.48 (d, J=6.1 Hz, 1H), 9.12 (s, 1H).

Mass spectrometric value (ESI-MS, m/z): 339 (M$^+$+1)

Example 3

N5-[1-(4-Chlorobenzyl)tetrahydro-1H-3-pyrrolyl]-5-isoquinolylamine

Tert-butyl 3-(5-isoquinolylamino)-1-pyrrolidinecarboxylate (intermediate 1) (62 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in 1 ml of acetonitrile. A solution (1 ml) of 4-chlorobenzylchloride (40 mg, 0.25 mmol) in acetonitrile was added dropwise to the solution at room temperature, and the mixture was stirred for additional 18 hr. Water (2 ml) was added to the reaction solution, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give the title compound (11 mg, 0.03 mmol).

$^1$H-NMR (CDCl$_3$, 400 MHz): 2.00-2.10 (m, 1H), 2.45-2.55 (m, 1H), 2.60-2.90 (m, 1H), 3.00-3.40 (m, 3H), 3.85-4.00 (m, 2H), 4.28-4.50 (m, 1H), 6.62 (d, J=7.3 Hz, 1H), 7.28-7.44 (m, 5H), 7.80-8.00 (m, 1H), 8.48 (d, J=6.1 Hz, 1H), 9.12 (s, 1H).

Mass spectrometric value (ESI-MS, m/z): 339 (M$^+$+1)

Example 4

N5-[1-(4-Fluorobenzyl)tetrahydro-1H-3-pyrrolyl]-5-isoquinolylamine

Tert-butyl 3-(5-isoquinolylamino)-1-pyrrolidinecarboxylate (intermediate 1) (62 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in 1 ml of acetonitrile. A solution (1 ml) of 4-fluorobenzylchloride (39 mg, 0.25 mmol) in acetonitrile was added dropwise to the solution at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give the title compound (17 mg, 0.053 mmol).

$^1$H-NMR (CDCl$_3$, 400 MHz): 1.80-2.10 (m, 1H), 2.40-2.53 (m, 1H), 2.57-2.75 (m, 1H), 2.90-3.25 (m, 3H), 3.75-3.88 (m, 2H), 4.21-4.31 (m, 1H), 6.64 (d, J=7.6 Hz, 1H), 7.03 (t, J=8.5 Hz, 2H), 7.30 (d, J=8.0 Hz, 1H), 7.35-7.43 (m, 3H), 7.65-7.78 (m, 1H), 8.47 (d, J=6.1 Hz, 1H), 9.12 (s, 1H).

Mass spectrometric value (ESI-MS, m/z): 322 (M$^+$+1)

Example 5

N5-[1-(2,6-Difluorobenzyl)tetrahydro-1H-3-pyrrolyl]-5-isoquinolylamine

Tert-butyl 3-(5-isoquinolylamino)-1-pyrrolidinecarboxylate (intermediate 1) (62 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in acetonitrile. A solution (1 ml) of 2,6-difluorobenzylchloride (40 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give the title compound (34 mg, 0.10 mmol).

$^1$H-NMR (CDCl$_3$, 400 MHz): 1.78-1.90 (m, 1H), 2.35-2.45 (m, 1H), 2.52-2.65 (m, 1H), 2.88-3.00 (m, 3H), 3.90 (s, 2H), 4.11-4.20 (m, 1H), 4.75-4.85 (m, 1H), 6.66 (d, J=7.6 Hz, 1H), 6.85-6.95 (m, 3H), 7.29 (d, J=8.3 Hz, 1H), 7.41 (t, J=7.9 Hz, 1H), 7.58 (d, J=6.1 Hz, 1H), 8.44 (d, J=6.1 Hz, 1H), 9.13 (s, 1H).

Mass spectrometric value (ESI-MS, m/z): 340 (M$^+$+1)

Example 6

N5-[1-(2,6-Dichlorobenzyl)tetrahydro-1H-3-pyrrolyl]-5-isoquinolylamine

Tert-butyl 3-(5-isoquinolylamino)-1-pyrrolidinecarboxylate (intermediate 1) (62 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in 1 ml of acetonitrile. A solution (1 ml) of 2,6-dichlorobenzylchloride (49 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give the title compound (22 mg, 0.059 mmol).

$^1$H-NMR (CDCl$_3$, 400 MHz): 1.83-1.95 (m, 1H), 2.33-2.43 (m, 1H), 2.65-2.75 (m, 1H), 2.95-3.15 (m, 3H), 4.09 (s, 2H), 4.13-4.24 (m, 1H), 4.90-5.05 (m, 1H), 6.67 (d, J=7.6 Hz, 1H), 7.17 (dd, J=7.8 Hz, 8.3 Hz, 1H), 7.28 (t, J=8.3 Hz, 1H), 7.33 (d, J=8.0 Hz, 1H), 7.41 (t, J=7.9 Hz, 1H), 7.61 (d, J=5.9 Hz, 1H), 8.45 (d, J=6.1 Hz, 1H), 9.11 (s, 1H).

Mass spectrometric value (ESI-MS, m/z): 373 (M$^+$+1)

Example 7

N-(5-Isoquinolyl)-N-[1-(4-methylbenzyl)tetrahydro-1H-3-pyrrolyl]amine

Tert-butyl 3-(5-isoquinolylamino)-1-pyrrolidinecarboxylate (intermediate 1) (62 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in 1 ml of acetonitrile. A solution (1 ml) of 4-methylbenzylchloride (40 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give the title compound (16 mg, 0.050 mmol).

Mass spectrometric value (ESI-MS, m/z): 318 (M$^+$+1)

Example 8

N5-[1-(4-Isopropylbenzyl)tetrahydro-1H-3-pyrrolyl]-5-isoquinolylamine

Tert-butyl 3-(5-isoquinolylamino)-1-pyrrolidinecarboxylate (intermediate 1) (62 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in 1 ml of acetonitrile. A solution (1 ml) of 4-isopropylbenzylchloride (42 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give the title compound (14 mg, 0.041 mmol).

$^1$H-NMR (CDCl$_3$, 400 MHz): 1.22 (d, J=6.9 Hz, 6H), 1.85-1.99 (m, 1H), 2.40-2.50 (m, 1H), 2.60-2.75 (m, 1H), 2.83-3.05 (m, 3H), 3.81 (s, 2H), 4.20-4.30 (m, 1H), 6.64 (d, J=7.8 Hz, 1H), 7.20 (d, J=8.1 Hz, 1H), 7.28-7.33 (m, 3H), 7.40 (t, J=7.8 Hz, 1H), 7.28-7.33 (m, 3H), 7.41 (t, J=7.8 Hz, 1H), 7.70-7.80 (m, 1H), 8.47 (d, J=6.1 Hz, 1H), 9.13 (s, 1H).

Mass spectrometric value (ESI-MS, m/z): 346 (M$^+$+1)

Example 9

N-(5-Isoquinolyl)-N-[1-(2-nitrobenzyl)tetrahydro-1H-3-pyrrolyl]amine

Tert-butyl 3-(5-isoquinolylamino)-1-pyrrolidinecarboxylate (intermediate 1) (62 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in 1 ml of acetonitrile. A solution (1 ml) of 2-nitrobenzylchloride (43 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give the title compound (27 mg, 0.076 mmol).

Mass spectrometric value (ESI-MS, m/z): 349 (M$^+$+1)

Example 10

N-(5-Isoquinolyl)-N-[1-(3-nitrobenzyl)tetrahydro-1H-3-pyrrolyl]amine

Tert-butyl 3-(5-isoquinolylamino)-1-pyrrolidinecarboxylate (intermediate 1) (62 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in 1 ml of acetonitrile. A solution (1 ml) of 3-nitrobenzylchloride (43 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give the title compound (27 mg, 0.076 mmol).

$^1$H-NMR (CDCl$_3$, 400 MHz): 1.78-1.90 (m, 1H), 2.40-2.57 (m, 2H), 2.72-2.79 (m, 1H), 2.85-2.96 (m, 2H), 3.77 (s, 2H), 4.14-4.24 (m, 1H), 4.55-4.67 (m, 1H), 6.69 (d, J=7.6 Hz, 1H), 7.31 (d, J=8.3 Hz, 1H), 7.41 (t, J=7.8 Hz, 1H), 7.49 (d, J=7.8 Hz, 1H), 7.58 (d, J=6.1 Hz, 1H), 7.69 (d, J=6.7 Hz, 1H), 8.11 (d, J=7.3 Hz, 1H), 8.23 (s, 1H), 8.47 (d, J=6.1 Hz, 1H), 9.14 (s, 1H).

Mass spectrometric value (ESI-MS, m/z): 349 (M$^+$+1)

Example 11

N-(5-Isoquinolyl)-N-[1-(4-nitrobenzyl)tetrahydro-1H-3-pyrrolyl]amine

Tert-butyl 3-(5-isoquinolylamino)-1-pyrrolidinecarboxylate (intermediate 1) (62 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in 1 ml of acetonitrile. A solution (1 ml) of 4-nitrobenzylchloride (43 mg, 0.25 mmol) in acetonitrile was added dropwise thereto at room temperature, and the mixture was stirred for additional 18 hr. Water (2 ml) was added to the reaction solution, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give the title compound (20 mg, 0.057 mmol).

$^1$H-NMR (CDCl$_3$, 400 MHz): 1.86-1.94 (m, 1H), 2.43-2.54 (m, 1H), 2.84-3.06 (m, 3H), 3.85 (s, 2H), 4.20-4.28 (m, 1H), 4.76-4.90 (m, 1H), 6.66 (d, J=7.6 Hz, 1H), 7.31 (d, J=8.3 Hz, 1H), 7.41 (t, J=7.9 Hz, 1H), 7.41 (t, J=7.9 Hz, 1H), 7.57 (d, J=8.5 Hz, 2H), 7.63 (d, J=5.8 Hz, 1H), 8.18 (d, J=8.8 Hz, 2H), 8.46 (d, J=5.8 Hz, 1H), 9.13 (s, 1H).

Mass spectrometric value (ESI-MS, m/z): 349 (M$^+$+1)

Example 12

N5-[1-(4-Chloro-2-nitrobenzyl)tetrahydro-1H-3-pyrrolyl]-5-isoquinolylamine

Tert-butyl 3-(5-isoquinolylamino)-1-pyrrolidinecarboxylate (intermediate 1) (62 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in 1 ml of acetonitrile. A solution (1 ml) of 4-chloro-2-nitrobenzylchloride (52 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give the title compound (37 mg, 0.106 mmol).

$^1$H-NMR (CDCl$_3$, 400 MHz): 1.80-1.92 (m, 1H), 2.30-2.55 (m, 2H), 2.70-2.90 (m, 3H), 3.99 (s, 2H), 4.35-4.43 (m, 1H), 4.68-4.78 (m, 1H), 6.65 (d, J=7.6 Hz, 1H), 7.30 (d, J=8.3 Hz, 1H), 7.41 (t, J=7.9 Hz, 1H), 7.50 (dd, J=2.2 Hz, 8.3 Hz, 1H), 7.55-7.69 (m, 1H), 7.68 (d, J=6.1 Hz, 1H), 7.80 (d, J=2.5 Hz, 1H), 8.49 (d, J=6.1 Hz, 1H), 9.13 (s, 1H).

Mass spectrometric value (ESI-MS, m/z): 383 (M$^+$+1)

Example 13

N-(5-Isoquinolyl)-N-[1-(2-pyridylmethyl)tetrahydro-1H-3-pyrrolyl]amine

Tert-butyl 3-(5-isoquinolylamino)-1-pyrrolidinecarboxylate (intermediate 1) (62 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in 1 ml of acetonitrile. A solution (1 ml) of 2-chloromethylpyridine (41 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give the title compound (10 mg, 0.033 mmol).

Mass spectrometric value (ESI-MS, m/z): 305 (M$^+$+1)

Example 14

N-(5-Isoquinolyl)-N-[1-(3-pyridylmethyl)tetrahydro-1H-3-pyrrolyl]amine

Tert-butyl 3-(5-isoquinolylamino)-1-pyrrolidinecarboxylate (intermediate 1) (62 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in 1 ml of acetonitrile. A solution (1 ml) of 3-chloromethylpyridine (41 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give the title compound (11 mg, 0.033 mmol).

Mass spectrometric value (ESI-MS, m/z): 305 ($M^+$+1)

Example 15

N-(5-Isoquinolyl)-N-[1-(4-pyridylmethyl)tetrahydro-1H-3-pyrrolyl]amine

Tert-butyl 3-(5-isoquinolylamino)-1-pyrrolidinecarboxylate (intermediate 1) (62 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in 1 ml of acetonitrile. A solution (1 ml) of 4-chloromethylpyridine (41 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give the title compound (11 mg, 0.033 mmol).

$^1$H-NMR (CDCl$_3$, 400 MHz): 1.90-2.00 (m, 1H), 2.40-2.67 (m, 2H), 2.88-3.25 (m, 3H), 3.77 (s, 2H), 4.20-4.30 (m, 1H), 4.82-4.98 (m, 1H), 6.66 (d, J=7.3 Hz, 1H), 7.28-7.35 (m, 4H), 7.42 (t, J=7.9 Hz, 1H) 7.65 (s, 1H), 8.48 (d, J=5.9 Hz, 1H), 8.54-8.60 (m, 1H), 9.13 (s, 1H).

Mass spectrometric value (ESI-MS, m/z): 305 ($M^+$+1)

Example 16

N5-[1-(2-Aminobenzyl)tetrahydro-1H-3-pyrrolyl]-5-isoquinolylamine

Tert-butyl 3-(5-isoquinolylamino)-1-pyrrolidinecarboxylate (intermediate 1) (62 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in 1 ml of acetonitrile. A solution (1 ml) of 2-nitrobenzylchloride (43 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 as an intermediate.

The intermediate was dissolved in 3 ml of 1 N hydrochloric acid at 80° C. Tin dichloride hydrate (Kanto Chemical Co., Inc., 113 mg, 0.50 mmol) was added little by little thereto, and the mixture was stirred at 80° C. for 3 hr. The reaction mixture was cooled to 0° C., and a 30% ammonia solution (1 ml) was added dropwise thereto. Ethylacetate was added, and the mixture was filtered through Celite. The filtrate was separated into an organic layer and an aqueous layer, and the aqueous layer was extracted twice with ethylacetate. The combined organic layer was dried over sodium sulfate and was concentrated to give a crude product. The crude product was further purified by column chromatography on alumina (alumina oxide 90 neutral) using chloroform/methanol (10:1) for development to give the title compound (20 mg, 0.063 mmol).

Mass spectrometric value (ESI-MS, m/z): 319 ($M^+$+1)

Example 17

N5-[1-(3-Aminobenzyl)tetrahydro-1H-3-pyrrolyl]-5-isoquinolylamine

Tert-butyl 3-(5-isoquinolylamino)-1-pyrrolidinecarboxylate (intermediate 1) (62 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in 1 ml of acetonitrile thereto. A solution (1 ml) of 3-nitrobenzylchloride (43 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give an intermediate.

The intermediate was dissolved in 3 ml of 1 N hydrochloric acid at 80° C. Tin dichloride hydrate (Kanto Chemical Co., Inc., 113 mg, 0.50 mmol) was added little by little thereto, and the mixture was stirred at 80° C. for 3 hr. The reaction mixture was cooled to 0° C., and 30% ammonia solution (1 ml) was added dropwise thereto. Ethylacetate was added, and the mixture was filtered through Celite. The filtrate was separated into an organic layer and an aqueous layer, and the aqueous layer was extracted twice with ethylacetate. The combined organic layer was dried over sodium sulfate and was concentrated to give a crude product. The crude product was further purified by column chromatography on alumina (alumina oxide 90 neutral) using chloroform/methanol (10:1) for development to give the title compound (17 mg, 0.053 mmol).

$^1$H-NMR (CDCl$_3$, 400 MHz): 1.80-1.94 (m, 1H), 2.38-2.48 (m, 1H), 2.52-2.62 (m, 1H), 2.75-2.86 (m, 1H), 2.87-3.02 (m, 1H), 3.64 (s, 2H), 4.14-4.24 (m, 1H), 4.75-4.90 (m, 1H), 6.58 (d, J=7.6 Hz, 1H), 6.66 (d, J=7.6 Hz, 1H), 6.70-6.75 (m, 2H), 7.09 (t, J=8.1 Hz, 1H), 7.29 (d, J=8.1 Hz, 1H), 7.41 (t, J=7.8 Hz, 1H), 7.59-7.66 (m, 1H), 8.46 (d, J=6.1 Hz, 1H), 9.13 (s, 1H).

Mass spectrometric value (ESI-MS, m/z): 319 (M$^+$+1)

Example 18

N5-[1-(4-Aminobenzyl)tetrahydro-1H-3-pyrrolyl]-5-isoquinolylamine

Tert-butyl 3-(5-isoquinolylamino)-1-pyrrolidinecarboxylate (intermediate 1) (62 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in 1 ml of acetonitrile. A solution (1 ml) of 4-nitrobenzylchloride (43 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give an intermediate.

The intermediate was dissolved in 3 ml of 1 N hydrochloric acid at 80° C. Tin dichloride hydrate (Kanto Chemical Co., Inc., 113 mg, 0.50 mmol) was added little by little thereto, and the mixture was stirred at 80° C. for 3 hr. The reaction mixture was cooled to 0° C., and a 30% ammonia solution (1 ml) was added dropwise thereto. Ethylacetate was added, and the mixture was filtrated through Celite. The filtrate was separated into an organic layer and an aqueous layer, and the aqueous layer was extracted twice with ethylacetate. The combined organic layer was dried over sodium sulfate and was concentrated to give a crude product. The crude product was further purified by column chromatography on alumina (alumina oxide 90 neutral) using chloroform/methanol (10:1) for development to give the title compound (12 mg, 0.037 mmol).

Mass spectrometric value (ESI-MS, m/z): 319 (M$^+$+1)

Example 19

N5-[1-(2-Amino-4-chlorobenzyl)tetrahydro-1H-3-pyrrolyl]-5-isoquinolylamine

Tert-butyl 3-(5-isoquinolylamino)-1-pyrrolidinecarboxylate (intermediate 1) (62 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in 1 ml of acetonitrile. A solution (1 ml) of 4-chloro-2-nitrobenzylchloride (50 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give an intermediate.

The intermediate was dissolved in 3 ml of 1 N hydrochloric acid at 80° C. Tin dichloride hydrate (Kanto Chemical Co., Inc., 113 mg, 0.50 mmol) was added little by little thereto, and the mixture was stirred at 80° C. for 3 hr. The reaction mixture was cooled to 0° C., and a 30% ammonia solution (1 ml) was added dropwise thereto. Ethylacetate was added, and the mixture was filtered through Celite. The filtrate was separated into an organic layer and an aqueous layer, and the aqueous layer was extracted twice with ethylacetate. The combined organic layer was dried over sodium sulfate and was concentrated to give a crude product. The crude product was further purified by column chromatography on alumina (alumina oxide 90 neutral) using chloroform/methanol (10:1) for development to give the title compound (24 mg, 0.068 mmol).

Mass spectrometric value (ESI-MS, m/z): 354 (M$^+$+1)

Example 20

N5-[1-(2-Chlorobenzyl)-3-piperidyl]-5-isoquinolylamine

Tert-butyl 3-(5-isoquinolylamino)-1-piperidinecarboxylate (intermediate 2) (66 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in 1 ml of acetonitrile. A solution (1 ml) of 2-chlorobenzylchloride (40 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give the title compound (19 mg, 0.054 mmol).

Mass spectrometric value (ESI-MS, m/z): 353 ($M^+$+1)

Example 21

N5-[1-(3-Chlorobenzyl)-3-piperidyl]-5-isoquinolylamine

Tert-butyl 3-(5-isoquinolylamino)-1-piperidinecarboxylate (intermediate 2) (66 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in 1 ml of acetonitrile; A solution (1 ml) of 3-chlorobenzylchloride (40 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give the title compound (23 mg, 0.066 mmol).

Mass spectrometric value (ESI-MS, m/z): 353 ($M^+$+1)

Example 22

N5-[1-(4-Chlorobenzyl)-3-piperidyl]-5-isoquinolylamine

Tert-butyl 3-(5-isoquinolylamino)-1-piperidinecarboxylate (intermediate 2) (66 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in 1 ml of acetonitrile. A solution (1 ml) of 4-chlorobenzylchloride (40 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give the title compound (24 mg, 0.066 mmol).

$^1$H-NMR (CDCl$_3$, 400 MHz): 1.48-2.00 (m, 5H), 2.38-3.05 (m, 3H), 3.40-4.20 (m, 3H), 6.63-6.78 (m, 1H), 7.23-7.52 (m, 7H), 8.48 (d, J=6.1 Hz, 1H), 9.12 (s, 1H).

Mass spectrometric value (ESI-MS, m/z): 353 ($M^+$+1)

Example 23

N-(1-Benzyl-3-piperidyl)-5-isoquinolylamine

Tert-butyl 3-(5-isoquinolylamino)-1-piperidinecarboxylate (intermediate 2) (66 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in 1 ml of acetonitrile. A solution (1 ml) of 4-fluorobenzylchloride (39 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give the title compound (18 mg, 0.057 mmol).

$^1$H-NMR (CDCl$_3$, 400 MHz): 1.40-2.05 (m, 5H), 2.25-2.98 (m, 3H), 3.37-4.10 (m, 3H), 6.65-6.80 (m, 1H), 7.24-7.58 (m, 9H), 8.47 (d, J=5.9 Hz, 1H), 9.12 (s, 1H).

Mass spectrometric value (ESI-MS, m/z): 318 (M$^+$+1)

Example 24

N5-[1-(2,6-Difluorobenzyl)-3-piperidyl]-5-isoquinolylamine

Tert-butyl 3-(5-isoquinolylamino)-1-piperidinecarboxylate (intermediate 2) (66 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added thereto, and the mixture was dissolved in 1 ml of acetonitrile. A solution (1 ml) of 2,6-difluorobenzylchloride (40 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give the title compound (25 mg, 0.071 mmol).

$^1$H-NMR (CDCl$_3$, 400 MHz): 1.48-2.20 (m, 5H), 2.45-3.22 (m, 3H), 3.75-4.25 (m, 3H), 6.70-6.80 (m, 1H), 6.90-7.02 (m, 2H), 7.24-7.30 (m, 3H), 7.43 (t, J=7.9 Hz, 1H), 7.59-7.66 (m, 1H), 8.46 (d, J=6.1 Hz, 1H), 9.12 (s, 1H).

Mass spectrometric value (ESI-MS, m/z): 354 (M$^+$+1)

Example 25

N5-[1-(2,6-Dichlorobenzyl)-3-piperidyl]-5-isoquinolylamine

Tert-butyl 3-(5-isoquinolylamino)-1-pyrrolidinecarboxylate (intermediate 1) (66 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added thereto, and the mixture was dissolved in 1 ml of acetonitrile. A solution (1 ml) of 2,6-dichlorobenzylchloride (49 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give the title compound (28 mg, 0.073 mmol).

$^1$H-NMR (CDCl$_3$, 400 MHz): 1.45-1.60 (m, 1H), 1.60-1.80 (m, 1H), 1.95-2.05 (m, 1H), 2.30-2.50 (m, 1H), 2.60-3.00 (m, 1H), 3.75-3.94 (m, 3H), 6.71 (d, J=8.1 Hz, 2H), 7.45 (t, J=8.0 Hz, 1H), 7.59-7.81 (m, 1H), 8.42 (d, J=6.1 Hz, 1H), 9.12 (s, 1H).

Mass spectrometric value (ESI-MS, m/z): 387 (M$^+$+1)

Example 26

N-(5-Isoquinolinyl)-N-[1-(4-methylbenzyl)-3-piperidyl]amine

Tert-butyl 3-(5-isoquinolylamino)-1-piperidinecarboxylate (intermediate 2) (66 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added thereto, and the mixture was dissolved in 1 ml of acetonitrile. A solution (1 ml) of 4-methylbenzylchloride (40 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give the title compound (20 mg, 0.060 mmol).

$^1$H-NMR (CDCl$_3$, 400 MHz): 1.48-2.00 (m, 5H), 2.32 (s, 3H), 2.25-2.80 (m, 3H), 3.35-4.00 (m, 3H), 6.65-6.80 (m, 1H), 7.10-7.18 (m, 3H), 7.22-7.30 (m, 2H), 7.41 (t, J=8.0 Hz, 1H), 7.50-7.60 (m, 1H), 8.47 (d, J=5.8 Hz, 1H), 9.12 (s, 1H).

Mass spectrometric value (ESI-MS, m/z): 332(M$^+$+1)

Example 27

N-(5-Isoquinolinyl)-N-[1-(4-isopropylbenzyl)-3-piperidyl]amine

Tert-butyl 3-(5-isoquinolylamino)-1-piperidinecarboxylate (intermediate 2) (66 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in 1 ml of acetonitrile. A solution (1 ml) of 4-isopropylbenzylchloride (42 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give the title compound (15 mg, 0.042 mmol).

$^1$H-NMR (CDCl$_3$, 400 MHz): 1.23 (d, J=7.0 Hz, 6H), 1.50-2.00 (m, 5H), 2.20-3.00 (m, 3H), 2.88 (dt, J=7.0 Hz, 13.4 Hz, 1H), 3.35-4.00 (m, 3H), 6.61-6.73 (m, 1H), 7.15-7.35 (m, 5H), 7.39 (t, J=7.6 Hz, 1H), 7.50-7.60 (m, 1H), 8.47 (d, J=5.9 Hz, 1H), 9.12 (s, 1H).

Mass spectrometric value (ESI-MS, m/z): 361 (M$^+$+1)

Example 28

N-(5-Isoquinolinyl)-N-[1-(2-nitrobenzyl)-3-piperidyl]amine

Tert-butyl 3-(5-isoquinolylamino)-1-piperidinecarboxylate (intermediate 2) (66 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in 1 ml of acetonitrile. A solution (1 ml) of 2-nitrobenzylchloride (43 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give the title compound (20 mg, 0.055 mmol).

$^1$H-NMR (CDCl$_3$, 400 MHz): 1.45-1.60 (m, 1H), 1.65-1.75 (m, 1H), 1.85-2.00 (m, 1H), 2.05-2.30 (m, 1H), 2.50-2.80 (m, 3H), 3.63-3.86 (m, 2H), 3.93-4.02 (m, 1H), 5.00-5.25 (m, 1H), 6.72 (d, J=7.8 Hz, 1H), 7.24-7.28 (m, 2H), 7.40-7.47 (m, 2H), 7.47-7.55 (m, 1H), 7.80 (d, J=7.8 Hz, 1H), 7.95-8.05 (m, 1H), 8.50 (d, J=6.1 Hz, 1H), 9.14 (s, 1H).

Mass spectrometric value (ESI-MS, m/z): 363 (M$^+$+1)

Example 29

N-(5-Isoquinolinyl)-N-[1-(3-nitrobenzyl)-3-piperidyl]amine

Tert-butyl 3-(5-isoquinolylamino)-1-piperidinecarboxylate (intermediate 2) (66 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in 1 ml of acetonitrile. A solution (1 ml) of 3-nitrobenzylchloride (43 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give the title compound (29 mg, 0.080 mmol).

Mass spectrometric value (ESI-MS, m/z): 363 (M$^+$+1)

Example 30

N-(5-Isoquinolinyl)-N-[1-(4-nitrobenzyl)-3-piperidyl]amine

Tert-butyl 3-(5-isoquinolylamino)-1-piperidinecarboxylate (intermediate 2) (66 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in 1 ml of acetonitrile. A solution (1 ml) of 4-nitrobenzylchloride (43 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give the title compound (26 mg, 0.075 mmol).

Mass spectrometric value (ESI-MS, m/z): 363 (M$^+$+1)

Example 31

N5-[1-(4-Chloro-2-nitrobenzyl)-3-piperidyl]-5-isoquinolylamine

Tert-butyl 3-(5-isoquinolylamino)-1-piperidinecarboxylate (intermediate 2) (66 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added thereto, and the mixture was dissolved in 1 ml of acetonitrile. A solution (1 ml) of 4-chloro-2-nitrobenzylchloride (52 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give the title compound (34 mg, 0.086 mmol).

$^1$H-NMR (CDCl$_3$, 400 MHz): 1.44-1.75 (m, 3H), 1.80-1.95 (m, 1H), 2.13-2.25 (m, 1H), 2.50-2.80 (m, 3H), 3.62-3.70 (m, 1H), 3.75-3.84 (m, 1H), 3.85-3.95 (m, 1H), 4.90-5.10 (m, 1H), 6.66-6.75 (m, 1H), 7.23-7.30 (m, 1H), 7.36-7.50 (m, 3H), 7.80 (s, 1H), 7.82-7.92 (m, 1H), 8.50 (d, J=6.1 Hz, 1H), 9.13 (s, 1H).

Mass spectrometric value (ESI-MS, m/z): 398 (M$^+$+1)

Example 32

N-(5-Isoquinolinyl)-N-[1-(2-pyridylmethyl)-3-piperidyl]amine

Tert-butyl 3-(5-isoquinolylamino)-1-piperidinecarboxylate (intermediate 2) (66 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in 1 ml of acetonitrile. A solution (1 ml) of 2-chloromethylpyridine (41 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give the title compound (23 mg, 0.072 mmol).

Mass spectrometric value (ESI-MS, m/z): 319 (M$^+$+1)

Example 33

N-(5-Isoquinolinyl)-N-[1-(3-pyridylmethyl)-3-piperidyl]amine

Tert-butyl 3-(5-isoquinolylamino)-1-piperidinecarboxylate (intermediate 2) (66 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in 1 ml of acetonitrile. A solution (1 ml) of 3-chloromethylpyridine (41 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give the title compound (14 mg, 0.044 mmol).

Mass spectrometric value (ESI-MS, m/z): 319 (M$^+$+1)

Example 34

N-(5-Isoquinolinyl)-N-[1-(4-pyridylmethyl)-3-piperidyl]amine

Tert-butyl 3-(5-isoquinolylamino)-1-piperidinecarboxylate (intermediate 2) (66 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in 1 ml of acetonitrile. A solution (1 ml) of 4-chloromethylpyridine (41 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give the title compound (16 mg, 0.050 mmol).

$^1$H-NMR (CDCl$_3$, 400 MHz): 1.56-1.90 (m, 4H), 2.40-2.70 (m, 3H), 2.70-2.85 (m, 1H), 3.50-3.75 (m, 2H), 3.80-

3.90 (m, 1H), 4.80-5.10 (m, 1H), 6.70-6.80 (m, 1H), 7.22-7.50 (m, 5H), 7.50-7.60 (m, 1H), 8.47 (d, J=6.1 Hz, 1H), 8.55 (s, 1H), 9.13 (s, 1H).

Mass spectrometric value (ESI-MS, m/z): 319 (M$^+$+1)

Example 35

N5-[1-(2-Aminobenzyl)-3-piperidyl]-5-isoquinolylamine

Tert-butyl 3-(5-isoquinolylamino)-1-piperidinecarboxylate (intermediate 2) (66 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in 1 ml of acetonitrile. A solution (1 ml) of 2-nitrobenzylchloride (43 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give an intermediate.

The intermediate was dissolved in 3 ml of 1 N hydrochloric acid at 80° C., tin dichloride hydrate (Kanto Chemical Co., Inc., 113 mg, 0.50 mmol) was added little by little thereto, and the mixture was stirred at 80° C. for 3 hr. The reaction mixture was cooled to 0° C., and a 30% ammonia solution (1 ml) was added dropwise thereto. Ethylacetate was added; and the mixture was filtrated through Celite. The filtrate was separated into an organic layer and an aqueous layer, and the aqueous layer was extracted twice with ethylacetate. The combined organic layer was dried over sodium sulfate and was concentrated to give a crude product. The crude product was further purified by column chromatography on alumina (alumina oxide 90 neutral) using chloroform/methanol (10:1) for development to give the title compound (18 mg, 0.054 mmol).

Mass spectrometric value (ESI-MS, m/z): 333 (M$^+$+1)

Example 36

N5-[1-(3-Aminobenzyl)-3-piperidyl]-5-isoquinolylamine

Tert-butyl 3-(5-isoquinolylamino)-1-piperidinecarboxylate (intermediate 2) (66 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in 1 ml of acetonitrile. A solution (1 ml) of 3-nitrobenzylchloride (43 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give an intermediate.

The intermediate was dissolved in 3 ml of 1 N hydrochloric acid at 80° C. Tin dichloride hydrate (Kanto Chemical Co., Inc., 113 mg, 0.50 mmol) was added little by little to the solution, and the mixture was stirred at 80° C. for 3 hr. The reaction mixture was cooled to 0° C., and a 30% ammonia solution (1 ml) was added dropwise thereto. Ethylacetate was added, and the mixture was filtrated through Celite. The filtrate was separated into an organic layer and an aqueous layer, and the aqueous layer was extracted twice with ethylacetate. The combined organic layer was dried over sodium sulfate and was concentrated to give a crude product. The crude product was further purified by column chromatography on alumina (alumina oxide 90 neutral) using chloroform/methanol (10:1) for development to give the title compound (22 mg, 0.066 mmol).

Mass spectrometric value (ESI-MS, m/z): 333 (M$^+$+1)

Example 37

N5-[1-(4-Aminobenzyl)-3-piperidyl]-5-isoquinolylamine

Tert-butyl 3-(5-isoquinolylamino)-1-piperidinecarboxylate (intermediate 2) (66 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in 1 ml of acetonitrile. A solution (1 ml) of 4-nitrobenzylchloride (43 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give an intermediate.

The intermediate was dissolved in 3 ml of 1 N hydrochloric acid at 80° C. Tin dichloride hydrate (Kanto Chemical Co., Inc., 113 mg, 0.50 mmol) was added little by little thereto, and the mixture was stirred at 80° C. for 3 hr. The reaction mixture was cooled to 0° C., and a 30% ammonia solution (1 ml) was added dropwise thereto. Ethylacetate was added, and the mixture was filtrated through Celite. The filtrate was separated into an organic layer and an aqueous layer, and the aqueous layer was extracted twice with ethylacetate. The combined organic layer was dried over sodium sulfate and was concentrated to give a crude product. The crude product was further purified by column chromatography on alumina (alumina oxide 90 neutral) using chloroform/methanol (10:1) for development to give the title compound (17 mg, 0.054 mmol).

Mass spectrometric value (ESI-MS, m/z): 333 ($M^+$+1)

Example 38

N5-[1-(2-Amino-4-chlorobenzyl)-3-piperidyl]-5-isoquinolylamine

Tert-butyl 3-(5-isoquinolylamino)-1-piperidinecarboxylate (intermediate 2) (66 mg, 0.20 mmol) was dissolved in 1 ml of chloroform. Trifluoroacetic acid (1 ml) was added thereto, and the mixture was stirred at room temperature for 3 hr. The reaction mixture was concentrated, potassium carbonate (Wako Kagaku Industry, Co., 69 mg, 0.50 mmol) was then added to the concentrate, and the mixture was dissolved in 1 ml of acetonitrile. A solution (1 ml) of 4-chloro-2-nitrobenzylchloride (50 mg, 0.25 mmol) in acetonitrile was added dropwise thereto at room temperature, and the mixture was stirred for additional 18 hr. Water (2 ml) was added thereto, and the mixture was then concentrated to remove a major part of acetonitrile. The aqueous layer was extracted three times with ethylacetate. The combined organic layer was dried over sodium sulfate and was concentrated. The resultant salt was further dissolved in a chloroform/methanol (10:1) solution, and the solution was filtered through a silica gel column with a short length. The filtrate was concentrated to give a crude product.

The crude product dissolved in chloroform was loaded on a silica gel column and developed with chloroform. The development was first carried out with chloroform only, subsequently with chloroform/methanol (20:1), and finally with chloroform/methanol (10:1) to collect a fraction having UV absorption with Rf=0.5 to give an intermediate.

The intermediate was dissolved in 3 ml of 1 N hydrochloric acid at 80° C. Tin dichloride hydrate (Kanto Chemical Co., Inc., 113 mg, 0.50 mmol) was added little by little thereto, and the mixture was stirred at 80° C. for 3 hr. The reaction mixture was cooled to 0° C., and a 30% ammonia solution (1 ml) was added dropwise thereto. Ethylacetate was added, and the mixture was filtrated through Celite. The filtrate was separated into an organic layer and an aqueous layer, and the aqueous layer was extracted twice with ethylacetate. The combined organic layer was dried over sodium sulfate and was concentrated to give a crude product. The crude product was further purified by column chromatography on alumina (alumina oxide 90 neutral) using chloroform/methanol (10:1) for development to give the title compound (18 mg, 0.049 mmol).

Mass spectrometric value (ESI-MS, m/z): 368 ($M^+$+1)

Example 39

N-(5-Isoquinolinyl)-N-[1-(1H-2-pyrrolylmethyl)-3-piperidyl]amine

Tert-butyl 3-(5-isoquinolylamino)-1-piperidinecarboxylate (intermediate 2) (66 mg, 0.20 mmol) was dissolved in 1 ml of chloroform. Trifluoroacetic acid (1 ml) was added thereto, and the mixture was stirred at room temperature for 3 hr. The reaction mixture was concentrated, diisopropylethylamine (65 mg, 0.50 mmol) was then added thereto, and the mixture was dissolved in 1 ml of acetonitrile. Pyrrole-2-carboxylic acid (28 mg, 0.25 mmol) was added thereto at room temperature, and, further, 1-ethyl-3-(3-dimethylaminopropyl)carbodiimide hydrochloride (51 mg, 0.30 mmol), 1-hydroxybenzotriazole (46 mg, 0.30 mmol), and dimethylaminopyridine (2 mg) were added thereto. The reaction mixture was stirred at room temperature for 18 hr. A saturated aqueous sodium hydrogencarbonate solution (2 ml) was then added thereto, and the mixture was extracted with ethylacetate. The organic layer was dried over anhydrous sodium sulfate, and the solvent was removed by evaporation under the reduced pressure to give a residue. The crude product in chloroform was loaded on a silica gel column and developed with chloroform/methanol. The development was first carried out with chloroform only, subsequently with chloroform/methanol (20:1), and finally with chloroform/methanol (10:1) to collect a fraction having UV absorption with Rf=0.5 to give an intermediate.

The intermediate was dissolved in tetrahydrofuran (1 ml). A borane-tetrahydrofuran complex (Kanto Chemical Co., Inc., 1 mol/l, tetrahydrofuran solution) (1 ml) was added dropwise thereto at 0° C. The reaction mixture was stirred at 60° C. for 3 hr and was then cooled to 0° C., and 2 ml of a 1 N aqueous solution of hydrochloric acid was added dropwise thereto. Further, the mixture was stirred at 60° C. for one hr, a saturated aqueous sodium hydrogencarbonate solution (1 ml) was then added thereto, and the mixture was extracted with ethylacetate. The organic layer was dried over anhydrous sodium sulfate, and the solvent was removed by evaporation under the reduced pressure to give a residue. The crude product in chloroform was loaded on a silica gel column and developed with chloroform/methanol. The development was first carried out with chloroform only, subsequently with chloroform/methanol (20:1), and finally with chloroform/methanol (10:1) to collect a fraction having UV absorption with Rf=0.5 to give the title compound (12 mg, 0.026 mmol).

$^1$H-NMR (CDCl$_3$, 400 MHz): 1.60-1.73 (m, 1H), 1.82-2.00 (m, 2H), 2.02-2.12 (m, 1H), 3.64-3.88 (m, 5H), 3.93-4.02 (m, 1H), 4.14-4.24 (m, 1H), 4.90-5.00 (m, 1H), 6.23 (s, 1H), 6.58 (s, 1H), 6.86 (d, J=7.6 Hz, 1H), 6.92 (s, 1H), 7.32 (d, J=8.3 Hz, 1H), 7.47 (t, J=7.9 Hz, 1H), 7.59 (s, 1H), 8.43 (d, J=6.1 Hz, 1H), 9.13 (s, 1H), 9.45-9.55 (s, 1H).

Mass spectrometric value (ESI-MS, m/z): 307 ($M^+$+1)

Example 40

N-(5-Isoquinolinyl)-N-[1-(1H-3-pyrrolylmethyl)-3-piperidyl]amine

Tert-butyl 3-(5-isoquinolylamino)-1-piperidinecarboxylate (intermediate 2) (66 mg, 0.20 mmol) was dissolved in 1 ml of chloroform. Trifluoroacetic acid (1 ml) was added thereto, and the mixture was stirred at room temperature for 3 hr. The reaction mixture was concentrated, diisopropylethylamine (65 mg, 0.50 mmol) was then added to the concentrate, and the mixture was dissolved in 1 ml of acetonitrile. Pyrrole-3-carboxylic acid (28 mg, 0.25 mmol) was added thereto at room temperature, and, further, 1-ethyl-3-(3-dimethylaminopropyl)carbodiimide hydrochloride (51 mg, 0.30 mmol), 1-hydroxybenzotriazole (46 mg, 0.30 mmol), and dimethylaminopyridine (2 mg) were added thereto. The reaction mixture was stirred at room temperature for 18 hr, a saturated aqueous sodium hydrogencarbonate solution (2 ml) was then added thereto, and the mixture was extracted with ethylacetate. The organic layer was dried over anhydrous sodium sulfate, and the solvent was removed by evaporation under the reduced pressure to give a residue. The crude product in chloroform was loaded on a silica gel column and developed with chloroform/methanol. The development was first carried out with chloroform only, subsequently with chloroform/methanol (20:1), and finally with chloroform/methanol (10:1) to collect a fraction having UV absorption with Rf=0.5 to give an intermediate.

The intermediate was dissolved in tetrahydrofuran (1 ml). A borane-tetrahydrofuran complex (Kanto Chemical Co., Inc., 1 mol/l, tetrahydrofuran solution) (1 ml) was added dropwise thereto at 0° C. The reaction mixture was stirred at 60° C. for 3 hr and was then cooled to 0° C., and 2 ml of a 1 N aqueous solution of hydrochloric acid was added dropwise thereto. Further, the mixture was stirred at 60° C. for one hr. A saturated aqueous sodium hydrogencarbonate solution (1 ml) was then added thereto, and the mixture was extracted with ethylacetate. The organic layer was dried over anhydrous sodium sulfate, and the solvent was removed by evaporation under the reduced pressure to give a residue. The crude product in chloroform was loaded on a silica gel column and developed with chloroform/methanol. The development was first carried out with chloroform only, subsequently with chloroform/methanol (20:1), and finally with chloroform/methanol (10:1) to collect a fraction having UV absorption with Rf=0.5 to give the title compound (15 mg, 0.049 mmol).

$^1$H-NMR (CDCl$_3$, 400 MHz): 1.55-1.70 (m, 1H), 1.75-1.88 (m, 1H), 1.90-2.10 (m, 2H), 3.62-3.90 (m, 6H), 4.08-4.16 (m, 1H), 6.40 (s, 1H), 6.70-6.85 (m, 2H), 7.18-7.24 (m, 1H), 7.28 (d, J=8.1 Hz, 1H), 7.38-7.46 (m, 1H), 7.56-7.64 (m, 1H), 8.42 (d, J=6.1 Hz, 1H), 8.66-8.82 (m, 1H), 9.12 (s, 1H).

Mass spectrometric value (ESI-MS, m/z): 307 (M$^+$+1)

Example 41

N-(5-Isoquinolinyl)-N-[1-(2-thienylmethyl)-3-piperidyl]amine

Tert-butyl 3-(5-isoquinolylamino)-1-piperidinecarboxylate (intermediate 2) (66 mg, 0.20 mmol) was dissolved in 1 ml of chloroform. Trifluoroacetic acid (1 ml) was added thereto, and the mixture was stirred at room temperature for 3 hr. The reaction mixture was concentrated, diisopropylethylamine (65 mg, 0.50 mmol) was then added to the concentrate, and the mixture was dissolved in 1 ml of acetonitrile. Thiophene-2-carboxylic acid (32 mg, 0.25 mmol) was added to the solution at room temperature, and, further, 1-ethyl-3-(3-dimethylaminopropyl)carbodiimide hydrochloride (51 mg, 0.30 mmol), 1-hydroxybenzotriazole (46 mg, 0.30 mmol), and dimethylaminopyridine (2 mg) were added thereto. The reaction mixture was stirred at room temperature for 18 hr, a saturated aqueous sodium hydrogencarbonate solution (2 ml) was then added thereto, and the mixture was extracted with ethylacetate. The organic layer was dried over anhydrous sodium sulfate, and the solvent was removed by evaporation under the reduced pressure to give a residue. The crude product in chloroform was loaded on a silica gel column and developed with chloroform/methanol. The development was first carried out with chloroform only, subsequently with chloroform/methanol (20:1), and finally with chloroform/methanol (10:1) to collect a fraction having UV absorption with Rf=0.5 to give an intermediate.

The intermediate was dissolved in tetrahydrofuran (1 ml), and 1 ml of a borane-tetrahydrofuran complex (Kanto Chemical Co., Inc., 1 mol/l, tetrahydrofuran solution) was added dropwise thereto at 0° C. The reaction mixture was stirred at 60° C. for 3 hr, and was then cooled to 0° C., and 2 ml of a 1 N aqueous solution of hydrochloric acid was added dropwise thereto. The mixture was stirred at 60° C. for additional one hr. A saturated aqueous sodium hydrogencarbonate solution (1 ml) was then added thereto, and the mixture was extracted with ethylacetate. The organic layer was dried over anhydrous sodium sulfate, and the solvent was removed by evaporation under the reduced pressure to give a residue. The crude product in chloroform was loaded on a silica gel column and developed with chloroform/methanol. The development was first carried out with chloroform only, subsequently with chloroform/methanol (20:1), and finally with chloroform/methanol (10:1) to collect a fraction having UV absorption with Rf=0.5 to give the title compound (7 mg, 0.022 mmol).

Mass spectrometric value (ESI-MS, m/z): 324 (M$^+$+1)

Example 42

N-(5-Isoquinolinyl)-N-[1-(3-thienylmethyl)-3-piperidyl]amine

Tert-butyl 3-(5-isoquinolylamino)-1-piperidinecarboxylate (intermediate 2) (66 mg, 0.20 mmol) was dissolved in 1 ml of chloroform. Trifluoroacetic acid (1 ml) was added thereto, and the mixture was stirred at room temperature for 3 hr. The reaction mixture was concentrated, diisopropylethylamine (65 mg, 0.50 mmol) was then added to the concentrate, and the mixture was dissolved in 1 ml of acetonitrile. Thiophene-3-carboxylic acid (32 mg, 0.25 mmol) was added to the solution at room temperature, and, further, 1-ethyl-3-(3-dimethylaminopropyl)carbodiimide hydrochloride (51 mg, 0.30 mmol), 1-hydroxybenzotriazole (46 mg, 0.30 mmol), and dimethylaminopyridine (2 mg) were added thereto. The reaction mixture was stirred at room temperature for 18 hr, a saturated aqueous sodium hydrogencarbonate solution (2 ml) was then added thereto, and the mixture was extracted with ethylacetate. The organic layer was dried over anhydrous sodium sulfate, and the solvent was removed by evaporation under the reduced pressure to give a residue. The crude product in chloroform was loaded on a silica gel column and developed with chloroform/methanol. The development was first carried out with chloroform only, subsequently with chloroform/methanol (20:1), and finally with chloroform/methanol (10:1) to collect a fraction having UV absorption with Rf=0.5 to give an intermediate.

The intermediate was dissolved in tetrahydrofuran (1 ml), and 1 ml of a borane-tetrahydrofuran complex (Kanto Chemical Co., Inc., 1 mol/l, tetrahydrofuran solution) was added dropwise thereto at 0° C. The reaction mixture was stirred at 60° C. for 3 hr, was then cooled to 0° C., and 2 ml of a 1 N aqueous solution of hydrochloric acid was added dropwise thereto. The mixture was further stirred at 60° C. for one hr. A saturated aqueous sodium hydrogencarbonate solution (1 ml) was then added thereto, and the mixture was extracted with ethylacetate. The organic layer was dried over anhydrous sodium sulfate, and the solvent was removed by evaporation under the reduced pressure to give a residue. The crude product in chloroform was loaded on a silica gel column and developed with chloroform/methanol. The development was first carried out with chloroform only, subsequently with chloroform/methanol (20:1), and finally with chloroform/methanol (10:1) to collect a fraction having UV absorption with Rf=0.5 to give the title compound (18 mg, 0.056 mmol).

Mass spectrometric value (ESI-MS, m/z): 324 (M$^+$+1)

Example 43

N-[1-(2-Furylmethyl)-3-piperidyl]-N-(5-isoquinolyl) amine

Tert-butyl 3-(5-isoquinolylamino)-1-piperidinecarboxylate (intermediate 2) (66 mg, 0.20 mmol) was dissolved in 1 ml of chloroform. Trifluoroacetic acid (1 ml) was added thereto, and the mixture was stirred at room temperature for 3 hr. The reaction mixture was concentrated, diisopropylethylamine (65 mg, 0.50 mmol) was then added to the concentrate, and the mixture was dissolved in 1 ml of acetonitrile. Furan-2-carboxylic acid (32 mg, 0.25 mmol) was added thereto at room temperature, and, further, 1-ethyl-3-(3-dimethylaminopropyl)carbodiimide hydrochloride (51 mg, 0.30 mmol), 1-hydroxybenzotriazole (46 mg, 0.30 mmol), and dimethylaminopyridine (2 mg) were added thereto. The reaction mixture was stirred at room temperature for 18 hr, a saturated aqueous sodium hydrogencarbonate solution (2 ml) was then added thereto, and the mixture was extracted with ethylacetate. The organic layer was dried over anhydrous sodium sulfate, and the solvent was removed by evaporation under the reduced pressure to give a residue. The crude product in chloroform was loaded on a silica gel column and developed with chloroform/methanol. The development was first carried out with chloroform only, subsequently with chloroform/methanol (20:1), and finally with chloroform/methanol (10:1) to collect a fraction having UV absorption with Rf=0.5 to give an intermediate.

The intermediate was dissolved in tetrahydrofuran (1 ml), and 1 ml of a borane-tetrahydrofuran complex (Kanto Chemical Co., Inc., 1 mol/l, tetrahydrofuran solution) was added dropwise thereto at 0° C. The reaction mixture was stirred at 60° C. for 3 hr, was then cooled to 0° C., and 2 ml of a 1 N aqueous solution of hydrochloric acid was added dropwise thereto. Further, the mixture was stirred at 60° C. for one hr, a saturated aqueous sodium hydrogencarbonate solution (1 ml) was then added thereto, and the mixture was extracted with ethylacetate. The organic layer was dried over anhydrous sodium sulfate, and the solvent was removed by evaporation under the reduced pressure to give a residue. The crude product in chloroform was loaded on a silica gel column and developed with chloroform/methanol. The development was first carried out with chloroform only, subsequently with chloroform/methanol (20:1), and finally with chloroform/methanol (10:1) to collect a fraction having UV absorption with Rf=0.5 to give the title compound (12 mg, 0.039 mmol).

Mass spectrometric value (ESI-MS, m/z): 308 ($M^+$+1)

Example 44

N-[1-(3-Furylmethyl)-3-piperidyl]-N-(5-isoquinolyl) amine

Tert-butyl 3-(5-isoquinolylamino)-1-piperidinecarboxylate (intermediate 2) (66 mg, 0.20 mmol) was dissolved in 1 ml of chloroform. Trifluoroacetic acid (1 ml) was added thereto, and the mixture was stirred at room temperature for 3 hr. The reaction mixture was concentrated, diisopropylethylamine (65 mg, 0.50 mmol) was then added to the concentrate, and the mixture was dissolved in 1 ml of acetonitrile. Furan-3-carboxylic acid (32 mg, 0.25 mmol) was added to the solution at room temperature, and, further, 1-ethyl-3-(3-dimethylaminopropyl)carbodiimide hydrochloride (51 mg, 0.30 mmol), 1-hydroxybenzotriazole (46 mg, 0.30 mmol), and dimethylaminopyridine (2 mg) were added thereto. The reaction mixture was stirred at room temperature for 18 hr, a saturated aqueous sodium hydrogencarbonate solution (2 ml) was then added thereto, and the mixture was extracted with ethylacetate. The organic layer was dried over anhydrous sodium sulfate, and the solvent was removed by evaporation under the reduced pressure to give a residue. The crude product in chloroform was loaded on a silica gel column and developed with chloroform/methanol. The development was first carried out with chloroform only, subsequently with chloroform/methanol (20:1), and finally with chloroform/methanol (10:1) to collect a fraction having UV absorption with Rf=0.5 to give an intermediate.

The intermediate was dissolved in tetrahydrofuran (1 ml), and 1 ml of a borane-tetrahydrofuran complex (Kanto Chemical Co., Inc., 1 mol/l, tetrahydrofuran solution) was added dropwise thereto at 0° C. The reaction mixture was stirred at 60° C. for 3 hr, was then cooled to 0° C., and 2 ml of a 1 N aqueous solution of hydrochloric acid was added dropwise thereto. The mixture was further stirred at 60° C. for one hr, a saturated aqueous sodium hydrogencarbonate solution (1 ml) was then added thereto, and the mixture was extracted with ethylacetate. The organic layer was dried over anhydrous sodium sulfate, and the solvent was removed by evaporation under the reduced pressure to give a residue. The crude product in chloroform was loaded on a silica gel column and developed with chloroform/methanol. The development was first carried out with chloroform only, subsequently with chloroform/methanol (20:1), and finally with chloroform/methanol (10:1) to collect a fraction having UV absorption with Rf=0.5 to give the title compound (18 mg, 0.059 mmol).

Mass spectrometric value (ESI-MS, m/z): 308 ($M^+$+1)

Example 45

(3S)-N5-[1-(3-Aminobenzyl)tetrahydro-1H-3-pyrrolyl]-5-isoquinolineamine

5-Hydroisoquinoline (Aldrich, 4.35 g, 30 mmol) and pyridine (3.16 g) were dissolved in anhydrous chloroform (50 ml), and trifluoromethansulfonic acid (10 g, 35 mmol) was added dropwise thereto at 0° C. The reaction mixture was stirred for 3 hr, and a saturated sodium hydrogencarbonate solution was then added thereto. The aqueous layer was extracted three times with ethylacetate. The combined organic layer was dried over sodium sulfate and was concentrated to give a crude product.

The crude product dissolved in chloroform was loaded on a silica gel column and developed with chloroform. The development was carried out with chloroform only to collect a fraction having UV absorption with Rf=0.7 to give intermediate A (7.55 g, 27 mmol).

Potassium carbonate (Wako Kagaku Industry, Co., 2.07 g, 15 mmol) was added to (3S)-(−)-3-(tert-butoxyamino)pyrrolidine (Tokyo Chemical Industry Co., Ltd., 1.86 g, 10 mmol), and the mixture was dissolved in 10 ml of acetonitrile. A solution (3 ml) of 3-nitrobenzylchloride (Tokyo Chemical Industry Co., Ltd., 1.88 g, 11 mmol) in acetonitrile was added dropwise thereto at room temperature, and the mixture was stirred for additional 18 hr. Water (10 ml) was added thereto, and the mixture was then concentrated to remove a major part of acetonitrile. The aqueous layer was extracted three times with ethylacetate. The combined organic layer was dried over sodium sulfate and was concentrated to give a crude product.

The crude product dissolved in chloroform was loaded on a silica gel column and developed with chloroform. The development was first carried out with chloroform only and subsequently with chloroform/methanol (20:1) to collect a fraction having UV absorption with Rf=0.6 as intermediate B (3.0 g, 9.3 mmol).

Intermediate B (1.0 g, 3.1 mmol) was dissolved in 2.5 mmol of chloroform, 2.5 ml of trifluoroacetic acid was added thereto, and the mixture was stirred at room temperature for 3 hr. The reaction mixture was concentrated under the reduced pressure to remove a major part of trifluoroacetic acid. The reaction mixture was then adjusted to pH 10 by the addition of a 3 N sodium hydroxide solution. The aqueous layer was extracted three times with ethylacetate. The combined organic layer was dried over sodium sulfate and was concentrated, the concentrate was then passed through an alumina (alumina oxide 90 neutral) column, to give a crude product.

Intermediate A (858 mg, 3.1 mmol), the above crude product, palladium acetate (Wako Kagaku Industry, Co., 113 mg, 0.50 mmol), racemic BINAP (Aldrich, 311 mg, 0.50 mmol), and cesium carbonate (Wako Kagaku Industry, Co., 1.63 g, 5 mmol) were suspended in anhydrous toluene (5 ml), and the suspension was stirred in an argon atmosphere at 80° C. for 18 hr. Ethylacetate (5 ml) was added thereto, and the mixture was filtrated through Celite. The filtrate was concentrated to give a crude product.

The crude product dissolved in chloroform was loaded on a silica gel column and developed with chloroform. The development was first carried out with chloroform only and subsequently with chloroform/methanol (20:1) to collect a fraction having UV absorption with Rf=0.6 as intermediate C (624 mg, 1.67 mmol).

Intermediate C (624 mg, 1.67 mmol) was dissolved in 3 ml of 1 N hydrochloric acid. Tin dichloride hydrate (Kanto Chemical Co., Inc., 1.13 g, 5 mmol) was added little by little thereto, and the mixture was stirred at 80° C. for 3 hr. The reaction mixture was cooled to 0° C., and a 30% ammonia solution (5 ml) was added dropwise thereto. Ethylacetate was added, and the mixture was filtrated through Celite. The filtrate was separated into an organic layer and an aqueous layer, and the aqueous layer was extracted twice with ethylacetate. The combined organic layer was dried over sodium sulfate and was concentrated to give a crude product. The crude product was further purified by column chromatography on alumina (alumina oxide 90 neutral) using chloroform/methanol (10:1) for development to give the title compound (488 mg, 1.53 mmol).

$^{1}$H-NMR (CDCl$_{3}$, 400 MHz): 1.80-1.94 (m, 1H), 2.38-2.48 (m, 1H), 2.52-2.62 (m, 1H), 2.75-2.86 (m, 1H), 2.87-3.02 (m, 1H), 3.64 (s, 3H), 4.14-4.24 (m, 1H), 4.75-4.90 (m, 1H), 6.58 (d, J=7.6 Hz, 1H), 6.66 (d, J=7.6 Hz, 1H), 6.70-6.75 (m, 2H), 7.09 (t, J=8.1 Hz, 1H), 7.29 (d, J=8.1 Hz, 1H), 7.41 (t, J=7.8 Hz, 1H), 7.59-7.66 (m, 1H), 8.46 (d, J=6.1 Hz, 1H), 9.13 (s, 1H).

Mass spectrometric value (ESI-MS, m/z): 319 (M$^{+}$+1)

Rotary power $[\alpha]^{25}_{D}$=+111 (C=0.25)

Example 46

(3R)-N5-[1-(3-Aminobenzyl)tetrahydro-1H-3-pyrrolyl]-5-isoquinolineamine

5-Hydroisoquinoline (Aldrich, 4.35 g, 30 mmol) and pyridine (3.16 g) were dissolved in anhydrous chloroform (50 ml). Trifluoromethansulfonic acid (10 g, 35 mmol) was added dropwise thereto at 0° C. The reaction mixture was stirred for 3 hr, and a saturated sodium hydrogencarbonate solution was then added thereto. The aqueous layer was extracted three times with ethylacetate. The combined organic layer was dried over sodium sulfate and was concentrated to give a crude product.

The crude product dissolved in chloroform was loaded on a silica gel column and developed with chloroform. The development was carried out with chloroform to collect a fraction having UV absorption with Rf=0.7 as intermediate A (7.55 g, 27 mmol).

Potassium carbonate (Wako Kagaku Industry, Co., 2.07 g, 15 mmol) was added to (3R)-(+)-3-(tert-butoxyamino)pyrrolidine (Tokyo Chemical Industry Co., Ltd., 1.86 g, 10 mmol), and the mixture was dissolved in 10 ml of acetonitrile. A solution (3 ml) of 3-nitrobenzylchloride (Tokyo Chemical Industry Co., Ltd., 1.88 g, 11 mmol) in acetonitrile was added dropwise thereto at room temperature, and the mixture was stirred for additional 18 hr. Water (10 ml) was added thereto, and the mixture was then concentrated to remove a major part of acetonitrile. The aqueous layer was extracted three times with ethylacetate. The combined organic layer was dried over sodium sulfate and was concentrated to give a crude product.

The crude product dissolved in chloroform was loaded on a silica gel column and developed with chloroform. The development was first carried out with chloroform and subsequently with chloroform/methanol (20:1) to collect a fraction having UV absorption with Rf=0.6 as intermediate B (2.7 g, 8.5 mmol).

Intermediate B (1.0 g, 3.1 mmol) was dissolved in 2.5 mmol of chloroform, 2.5 ml of trifluoroacetic acid was added thereto, and the mixture was stirred at room temperature for 3 hr. The reaction mixture was concentrated under the reduced pressure to remove a major part of trifluoroacetic acid. The reaction mixture was then adjusted to pH 10 by the addition of a 3 N sodium hydroxide solution. The aqueous layer was extracted three times with ethylacetate. The combined organic layer was dried over sodium sulfate and was concentrated, the concentrate was further passed through an alumina (alumina oxide 90 neutral) column, to give a crude product.

Intermediate A (858 mg, 3.1 mmol), the above crude product, palladium acetate (Wako Kagaku Industry, Co., 113 mg, 0.50 mmol), racemic BINAP (Aldrich, 311 mg, 0.50 mmol), and cesium carbonate (Wako Kagaku Industry, Co., 1.63 g, 5 mmol) were suspended in anhydrous toluene (5 ml), and the suspension was stirred in an argon atmosphere at 80° C. for 18 hr. Ethylacetate (5 ml) was added, and the mixture was filtrated through Celite, and the filtrate was concentrated to give a crude product.

The crude product dissolved in chloroform was loaded on a silica gel column and developed with chloroform. The development was first carried out with chloroform only and subsequently with chloroform/methanol (20:1) to collect a fraction having UV absorption with Rf=0.6 as intermediate C (629 mg, 1.68 mmol).

Intermediate C (624 mg, 1.67 mmol) was dissolved in 3 ml of 1 N hydrochloric acid, tin dichloride hydrate (Kanto Chemical Co., Inc., 1.13 g, 5 mmol) was added little by little thereto, and the mixture was stirred at 80° C. for 3 hr. The reaction mixture was cooled to 0° C., and a 30% ammonia solution (5 ml) was added dropwise thereto. Ethylacetate was added, and the mixture was filtrated through Celite. The filtrate was separated into an organic layer and an aqueous layer, and the aqueous layer was extracted twice with ethylacetate. The combined organic layer was dried over sodium sulfate and was concentrated to give a crude product. The crude product was further purified by column chromatography on alumina (alumina oxide 90 neutral) using chloroform/methanol (10:1) for development to give the title compound (462 mg, 1.45 mmol).

¹H-NMR (CDCl₃, 400 MHz): 1.80-1.94 (m, 1H), 2.38-2.48 (m, 1H), 2.52-2.62 (m, 1H), 2.75-2.86 (m, 1H), 2.87-3.02 (m, 1H), 3.64 (s, 3H), 4.14-4.24 (m, 1H), 4.75-4.90 (m, 1H), 6.58 (d, J=7.6 Hz, 1H), 6.66 (d, J=7.6 Hz, 1H), 6.70-6.75 (m, 2H), 7.09 (t, J=8.1 Hz, 1H), 7.29 (d, J=8.1 Hz, 1H), 7.41 (t, J=7.8 Hz, 1H), 7.59-7.66 (m, 1H), 8.46 (d, J=6.1 Hz, 1H), 9.13 (s, 1H).

Mass spectrometric value (ESI-MS, m/z): 319 (M⁺+1)

Rotary power $[\alpha]^{25}_D = -103$ (C=0.25)

The compounds prepared in Examples 1 to 46 were treated in a hydrochloric acid-methanol solution and were then concentrated, and the concentrates were washed with ether to give corresponding hydrochlorides.

The compounds prepared in Examples 1 to 46 and intermediates 1 and 2 had the following respective chemical structures.

Example 1

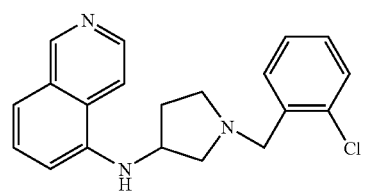

Example 2

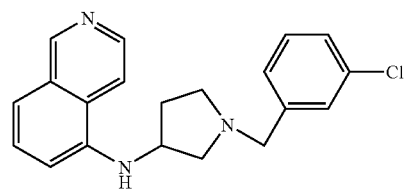

Example 3

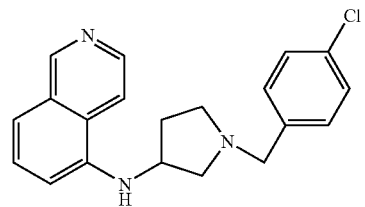

Example 4

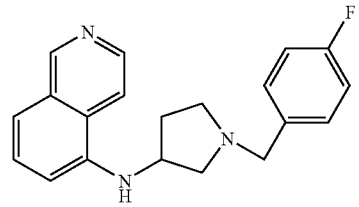

Example 5

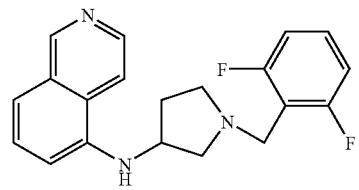

Example 6

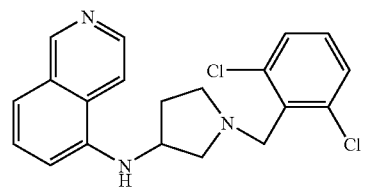

-continued

Example 7

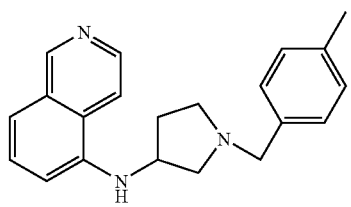

Example 8

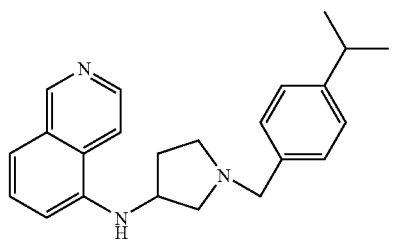

Example 9

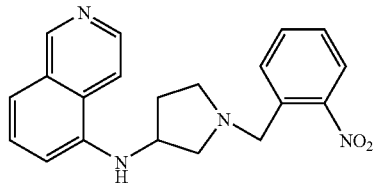

Example 10

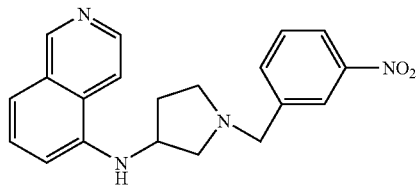

Example 11

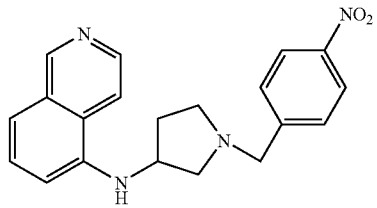

Example 12

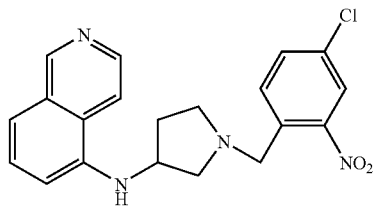

Example 13

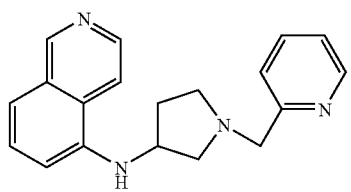

-continued

Example 14

Example 15

Example 16

Example 17

Example 18

Example 19

Example 20

Example 21

-continued

Example 22

Example 23

Example 24

Example 25

Example 26

Example 27

Example 28

-continued
Example 29
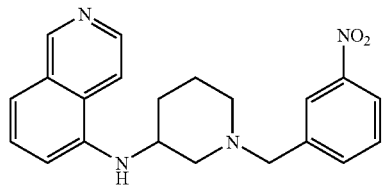
Example 30
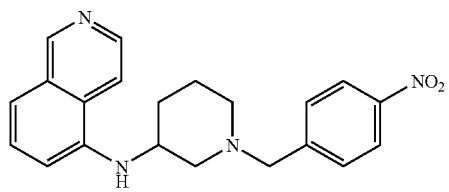
Example 31
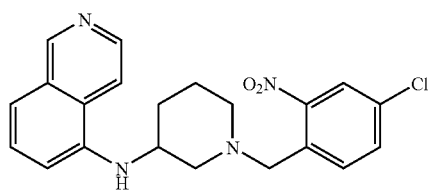
Example 32
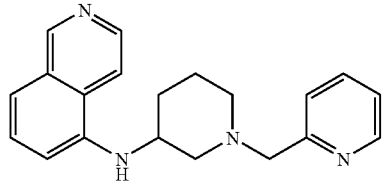
Example 33
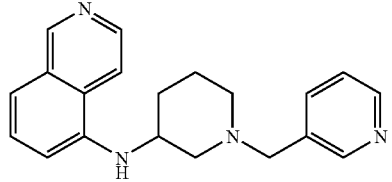
Example 34
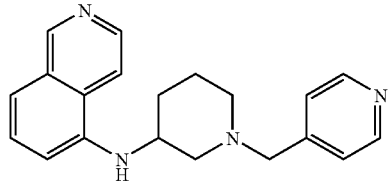
Example 35
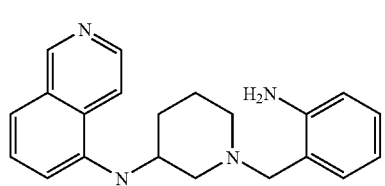
Example 36
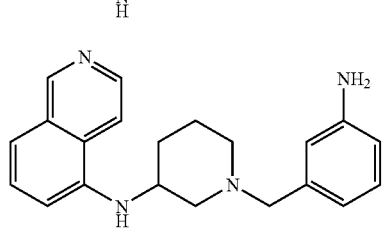
-continued
Example 37
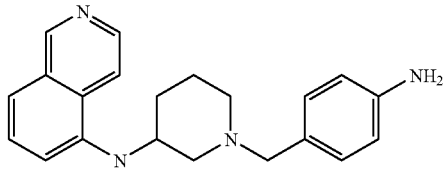
Example 38
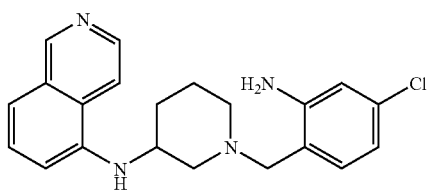
Example 39
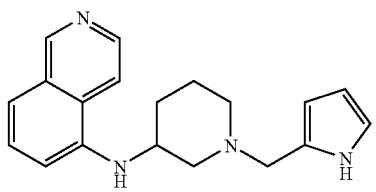
Example 40
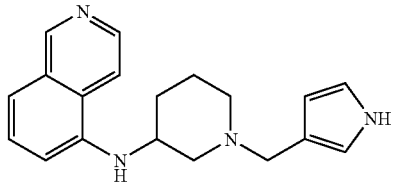
Example 41
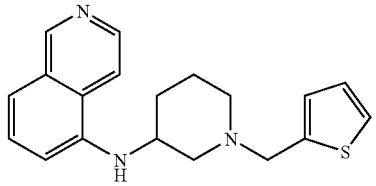
Example 42
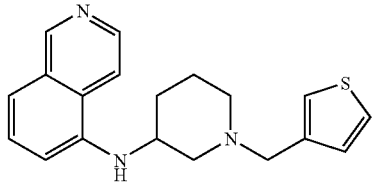
Example 43
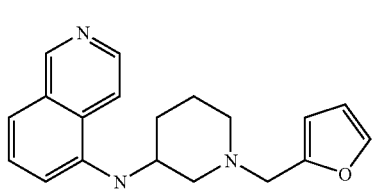
Example 44
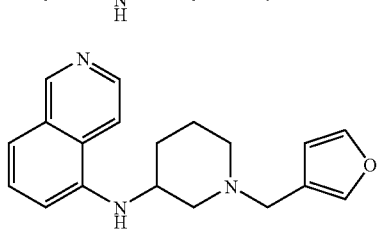

-continued

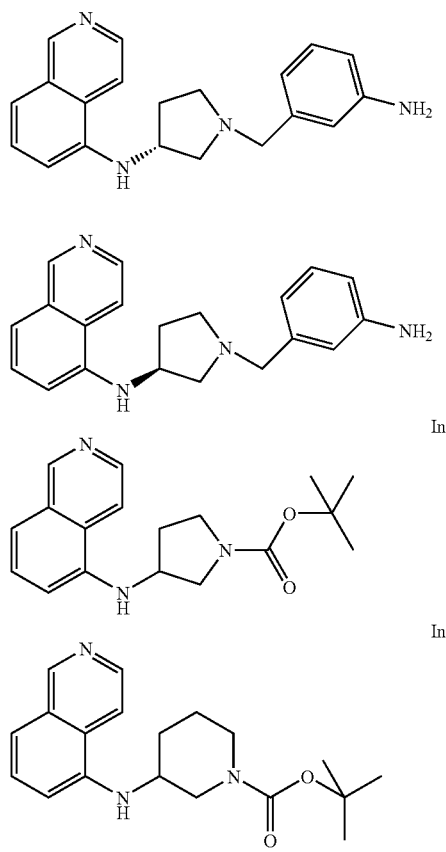

Example 45

Example 46

Intermediate 1

Intermediate 2

Pharmacological Test Example 1

Rho Kinase Inhibitory Activity

Recombinant Rho kinase was prepared according to the disclosure of Japanese Patent Laid-Open No. 113187/1998, i.e., by infecting insect cells with baculovirus, into which cDNA coding fused protein composed of bovine Rho kinase catalytic region and glutathione S-transferase had been incorporated, and allowing the insect cells to produce the recombinant Rho kinase. A substrate (ribosomal S6 kinase substrate, S6 231-239) was phosphorylated by adding the Rho kinase, together with ATP ($\gamma^{32}$P-ATP) of which phosphorus at the γ-position had been labeled with a radioisotope, to the substrate. This permits the substrate to be labeled with the radioisotope.

Thereafter, the substrate was adsorbed to a filter paper. ATP was washed away with a phosphoric acid solution, and the amount of the phosphorylated substrate was then measured with a liquid scintillation counter.

The antienzymatic activity of a test compound was determined by adding the test samples before the enzymatic reaction, determining the percentage phosphorylation inhibition of the substrate, and determining, as $IC_{50}$, a concentration of the test compound necessary for inhibiting the phosphorylation by 50%.

The results are shown in the table below.

| Test compound | IC50 (μM) |
|---|---|
| Example 1 | 0.099 |
| 2 | 0.063 |
| 3 | 0.066 |
| 4 | 0.093 |
| 5 | 0.073 |
| 6 | 0.14 |
| 7 | 0.096 |
| 8 | 0.20 |
| 9 | 0.57 |
| 10 | 0.20 |
| 11 | 0.66 |
| 12 | 1.3 |
| 13 | 0.48 |
| 14 | 0.59 |
| 15 | 1.1 |
| 16 | 0.21 |
| 17 | 0.28 |
| 18 | 0.23 |
| 19 | 0.24 |
| 20 | 0.21 |
| 21 | 0.27 |
| 22 | 0.19 |
| 23 | 0.24 |
| 24 | 0.23 |
| 25 | 1.2 |
| 26 | 0.18 |
| 27 | 0.53 |
| 28 | 0.58 |
| 29 | 1.9 |
| 30 | 1.8 |
| 31 | 2.3 |
| 32 | 1.3 |
| 33 | 1.0 |
| 34 | 1.5 |
| 35 | 0.27 |
| 36 | 0.31 |
| 37 | 0.29 |
| 38 | 0.40 |
| 39 | 0.023 |
| 40 | 0.67 |
| 41 | 0.19 |
| 42 | 0.031 |
| 43 | 0.20 |
| 44 | 0.11 |
| 45 | 0.31 |
| 46 | 0.023 |

Pharmacological Test Example 2

Leukocyte Migration Inhibitory Activity

Mouse-derived CCR2 overexpressing human-derived histiocyte lymphoma (U937/CCR2), was suspended in a 0.1% BSA-containing RPMI 1640 medium, to which a test compound had been added ($5\times10^6$/ml), and the suspension was incubated for 20 min. A chemical solution (500 μl) (0.1% BSA-containing RPMI 1640 medium DMSO 1%), to which an MCP-1 ligand (1 μM) and the test compound had been added, was added to a 24-well plate. CHEMOTAXICELL was put thereon, and 200 μl of the cell suspension was added to the top layer, followed by migration under a 5% $CO_2$ atmosphere at 37° C. for one hr. The number of cells, which had migrated to the lower chamber, was counted with a particle count analyzer (CDA-500, SYSMEX CORPORATION), and the percentage migration inhibition was calculated by the following equation:

Migration inhibition (%)=(1−number of migrated cells in the presence of test compound/number of migrated cells in the absence of test compound)× 100

The results are shown in the table below.

Test Compound

| (Concentration 10 μg/ml) | Migration inhibition (%) |
| --- | --- |
| Example 1 | 86 |
| 2 | 90 |
| 3 | 101 |
| 4 | 98 |
| 5 | 93 |
| 7 | 103 |
| 16 | 99 |
| 17 | 94 |
| 18 | 94 |
| 19 | 82 |
| 20 | 69 |
| 21 | 97 |
| 22 | 80 |
| 45 | 74 |
| 46 | 104 |

Pharmacological Test Example 3

Ex Vivo Experiment

Water or a solution of a hydrochloride salt of a test compound (30 mg/kg) in physiological saline was orally administered to SD rats (N=4). The blood samples were collected 3 hr after the administration. The serum was diluted 8 times with physiological saline and was added to Rho kinase, substrate, and labeled ATP according to the method described in Pharmacological Test Example 1, and the amount of the phosphorylated substrate was determined. Rho kinase inhibition was calculated according to the following equation:

Inhibition (%)=(1−amount of substrate in the case of test compound administration/amount of substrate in the case of water administration)×100

The results are shown in the table below.

| Test compound | Inhibition (%) |
| --- | --- |
| Example 17 | 57 |
| Example 45 | 17* |
| Example 46 | 42* |

(*Blood collection 4 hr after administration)

Pharmacological Test Example 4

Proteinuria Amelioration Activity for Anti-GBM Nephritis Model Using WKY Rats An anti-GBM antibody produced by immunizing domestic rabbits with a rat-derived GBM fraction was caudointravenously administered to WKY male rats of 8 weeks old to induce nephritis. For 3 days from the time 24 hr after the administration of the antibody, a solution of each of the hydrochlorides prepared in Examples 45 and 46 in purified water was orally administered at a dose of 30 mg/kg twice a day. Three days after the administration of the antibody, twenty-four-hours urine was collected to determine the protein level of urine. The mean of urine protein level and the standard error for 6 rats are shown in the table below.

| Group | Protein level of urine (mg/kg, body weight) |
| --- | --- |
| Control group | 491.9 ± 48.1 |
| Example 45 administration group | 91.2 ± 21.5 |
| Example 46 administration group | 73.6 ± 9.1 |
| Normal group | 66.3 ± 8.4 |

Four days after the administration of the antibody, the rats were sacrificed by exsanguination, and the kidney was then harvested and was fixed in 4% paraformaldehyde to prepare a specimen for staining. Next, the specimen thus obtained was immunostained using a mouse-anti-rat macrophage monoclonal antibody (ED-1). The number of ED-1 positive cells per glomerulus was counted. The mean of the number of ED-1 positive cells and the standard error for 6 rats in each group are shown in the table below.

| Group | Number of cells |
| --- | --- |
| Control group | 4.80 ± 0.75 |
| Example 45 administration group | 2.20 ± 0.65 |
| Example 46 administration group | 1.38 ± 0.68 |
| Normal group | 0.00 ± 0.00 |

Likewise, an anti-GBM antibody was caudointravenously administered to WKY male rats of 7 weeks old to induce nephritis. For 4 weeks from the time 24 hr after the administration of the antibody, a solution of the hydrochloride prepared in each of Examples 45 and 46 in purified water was orally administered at a dose of 30 mg/kg twice a day. Four weeks after the administration of the antibody, twenty-four-hours urine was collected to determine the protein level of urine. The mean of urine protein level and the standard error for 6 rats are shown in the table below.

| Group | Protein level of urine (mg/kg, body weight) |
| --- | --- |
| Control group | 1559.4 ± 121.7 |
| Example 45 administration group | 779.4 ± 133.9 |
| Example 46 administration group | 327.6 ± 55.2 |
| Normal group | 68.9 ± 4.0 |

Pharmacological Test Example 5

Blood Pressure Depression Activity

Spontaneously hypertensive male rats (SHR, Charles River Japan, Inc.) of 15 weeks old were provided. A solution of a hydrochloride of a compound of Example 45 or 46 (30 mg/kg) in purified water was orally administered to the rats. The systolic pressure of SHR was measured immediately before the administration of the test compound and 3 to 4 hr after the administration of the test compound. The percentage blood pressure depression was calculated by the following equation:

Blood pressure depression (%)={(blood pressure before administration of test compound−blood pressure after administration of test compound)/blood pressure before administration of test compound}×100

The results were as shown in the table below. The blood pressure depression was expressed in terms of the percentage blood pressure depression and the standard error for four SHRs.

| Test compound | Blood pressure depression (%) |
|---|---|
| Example 45 | 10.2 ± 3.1 |
| Example 46 | 25.1 ± 4.4 |

The invention claimed is:

1. A compound represented by formula (I) or a pharmaceutically acceptable salt or solvate thereof:

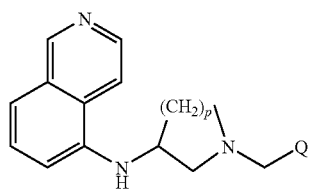

(I)

wherein Q represents a cyclic group selected from phenyl, pyridyl, pyrrolyl, thienyl, and furyl; one or two hydrogen atoms on the cyclic group are optionally substituted by a substituent selected from the group consisting of a halogen atom, $C_{1-4}$ alkyl, nitro, and amino; and p is 2.

2. The compound according to claim 1, wherein Q represents a cyclic group selected from phenyl, 2-chlorophenyl, 3-chlorophenyl, 4-chlorophenyl, 4-fluorophenyl, 2,6-difluorophenyl, 2,6-dichlorophenyl, 4-methylphenyl, 4-isopropylphenyl, 2-nitrophenyl, 3-nitrophenyl, 4-nitrophenyl, 4-chloro-2-nitrophenyl, 2-pyridyl, 3-pyridyl, 4-pyridyl, 2-aminophenyl, 3-aminophenyl, 4-aminophenyl, 2-amino-4-chlorophenyl, 1H-2-pyrrolyl, 1H-3-pyrrolyl, 2-thienyl, 3-thienyl, 2-furyl, and 3-furyl.

3. The compound according to claim 1, wherein Q represents 3-nitrophenyl or 3-aminophenyl.

4. The compound according to claim 1, which is selected from the group consisting of:
(1) N5-[1-(2-chlorobenzyl)tetrahydro-1H-3 -pyrrolyl]-5-isoquinolylamine;
(2) N5-[1-(3-chlorobenzyl)tetrahydro-1H-3-pyrrolyl]-5-isoquinolylamine;
(3) N5-[1-(4-chlorobenzyl)tetrahydro-1H-3-pyrrolyl]-5-isoquinolylamine;
(4) N5-[1-(4-fluorobenzyl)tetrahydro-1H-3-pyrrolyl]-5-isoquinolylamine;
(5) N5-[1-(2,6-difluorobenzyl)tetrahydro-1H-3-pyrrolyl]-5-isoquinolylamine;
(6) N5-[1-(2,6-dichlorobenzyl)tetrahydro-1H-3-pyrrolyl]-5-isoquinolylamine;
(7) N-(5-isoquinolyl)-N-[1-(4-methylbenzyl)tetrahydro-1H-3-pyrrolyl]amine;
(8) N5-[1-(4-isopropylbenzyl)tetrahydro-1H-3-pyrrolyl]-5-isoquinolylamine;
(9) N-(5-isoquinolyl)-N-[1-(2-nitrobenzyl)tetrahydro-1H-3-pyrrolyl]amine;
(10) N-(5-isoquinolyl)-N-[1-(3-nitrobenzyl)tetrahydro-1H-3-pyrrolyl]amine;
(11) N-(5-isoquinolyl)-N-[1-(4-nitrobenzyl)tetrahydro-1H-3-pyrrolyl]amine;
(12) N5-[1-(4-chloro-2-nitrobenzyl)tetrahydro-1H-3-pyrrolyl]-5-isoquinolylamine;
(13) N-(5-isoquinolyl)-N-[1-(2-pyridylmethyl)tetrahydro-1H-3-pyrrolyl]amine;
(14) N-(5-isoquinolyl)-N-[1-(3-pyridylmethyl)tetrahydro-1H-3-pyrrolyl]amine;
(15) N-(5-isoquinolyl)-N-[1-(4-pyridylmethyl)tetrahydro-1H-3-pyrrolyl]amine;
(16) N5-[1-(2-aminobenzyl)tetrahydro-1H-3-pyrrolyl]-5-isoquinolylamine;
(17) N5-[1-(3-aminobenzyl)tetrahydro-1H-3-pyrrolyl]-5-isoquinolylamine;
(18) N5-[1-(4-aminobenzyl)tetrahydro-1H-3-pyrrolyl]-5-isoquinolylamine;
(19) N5-[1-(2-amino-4-chlorobenzyl)tetrahydro-1H-3-pyrrolyl]-5-isoquinolylamine;
(45) (3S)-N5-[1-(3-aminobenzyl)tetrahydro-1H-3-pyrrolyl]-5-isoquinolineamine; and
(46) (3R)-N5-[1-(3-aminobenzyl)tetrahydro-1H-3-pyrrolyl]-5-isoquinolineamine.

5. The compound according to claim 1, which is selected from (3S)-N5-[1-(3-aminobenzyl)tetrahydro-1H-3-pyrrolyl]-5-isoquinolineamine and (3R)-N5-[1-(3-aminobenzyl)tetrahydro-1H-3-pyrrolyl]-5-isoquinolineamine and a mixture thereof.

6. A pharmaceutical composition comprising a compound according to claim 1 or a pharmaceutically acceptable salt or solvate thereof.

7. The pharmaceutical composition according to claim 6, for the treatment of a disease mediated by Rho kinase.

8. The pharmaceutical composition according to claim 7, wherein the disease mediated by Rho kinase is selected from the group consisting of hypertension, asthma including bronchial asthma, angina pectoris, cerebrovascular contraction, peripheral circulatory disorder, threatened premature birth, glaucoma, constriction of visual field, pollakiuria, cancer, invasion/metastasis of cancer, arteriosclerosis, retinopathy, immune response, inflammation, autoimmune diseases, cerebral dysfunction, osteoporosis, microbism, chronic renal failure, chronic nephritis, diabetic nephropathy, IgA nephropathia, thrombosis-related diseases, rheumatism, impotence, and fibrosis.

9. A method of producing a medicament, which comprises combining a compound according to claim 1 or a pharmaceutically acceptable salt or solvate thereof with a pharmaceutically acceptable carrier, for the manufacture of a medicament in the treatment of diseases mediated by Rho kinase.

10. The method according to claim 9, wherein the disease mediated by Rho kinase is selected from the group consisting of hypertension, asthma including bronchial asthma, angina pectoris, cerebrovascular contraction, peripheral circulatory disorder, threatened premature birth, glaucoma, constriction of visual field, pollakiuria, cancer, invasion/metastasis of cancer, arteriosclerosis, retinopathy, immune response, inflammation, autoimmune diseases, cerebral dysfunction, osteoporosis, microbism, chronic renal failure, chronic nephritis, diabetic nephropathy, IgA nephropathia, thrombosis-related diseases, rheumatism, impotence, and fibrosis.

11. A method for treating a disease mediated by Rho kinase, comprising the step of administering a therapeutically effective amount of a compound according to claim 1 or a pharmaceutically acceptable salt or solvate thereof together with a pharmaceutically acceptable carrier, to a mammal wherein the disease is hypertension.

* * * * *